United States Patent
Hoffman (12)

(10) Patent No.: US 6,287,264 B1
(45) Date of Patent: Sep. 11, 2001

(54) SYSTEM FOR MEASURING RESPIRATORY FUNCTION

(75) Inventor: Andrew Hoffman, Boston, MA (US)

(73) Assignee: The Trustees of Tufts College, Medford, MA (US)

( * ) Notice: Subject to any disclaimer, the term of this patent is extended or adjusted under 35 U.S.C. 154(b) by 0 days.

(21) Appl. No.: 09/298,352

(22) Filed: Apr. 23, 1999

(51) Int. Cl.⁷ .................................................. A61B 5/02

(52) U.S. Cl. .................................... 600/538; 600/529

(58) Field of Search .................................... 600/529, 534, 600/538

(56) References Cited

U.S. PATENT DOCUMENTS

| | | | |
|---|---|---|---|
| 3,677,261 | 7/1972 | Day | 128/2.1 Z |
| 4,036,217 | 7/1977 | Ito et al. | 128/2.08 |
| 4,036,222 | 7/1977 | Gillard et al. | 128/2.08 |
| 4,305,400 | 12/1981 | Logan | 128/670 |
| 4,314,563 | 2/1982 | Wheeler | 128/693 |
| 4,671,297 | 6/1987 | Schulze, Jr. | 128/716 |
| 4,777,962 | 10/1988 | Watson et al. | 128/716 |
| 4,796,639 * | 1/1989 | Snow et al. | 600/538 |
| 4,960,118 | 10/1990 | Pennock | 128/200 |
| 5,038,773 | 8/1991 | Norlien et al. | 128/205 |
| 5,273,036 | 12/1993 | Kronberg et al. | 128/633 |
| 5,316,010 | 5/1994 | Brown | 128/721 |
| 5,331,968 | 7/1994 | Williams et al. | 128/721 |
| 5,379,777 | 1/1995 | Lomask | 128/716 |
| 5,513,647 * | 5/1996 | Castile | 600/538 |
| 5,513,648 | 5/1996 | Jackson | 128/721 |
| 5,520,192 | 5/1996 | Kitney et al. | 128/716 |
| 5,522,397 | 6/1996 | Vermaak | 128/720 |
| 5,582,182 | 12/1996 | Hillsman | 128/716 |
| 5,598,838 | 2/1997 | Servidio et al. | 128/204 |
| 5,680,871 | 10/1997 | Ganshorn | 128/204 |
| 5,857,459 | 1/1999 | Snow et al. | 128/204 |
| 5,984,872 * | 11/1999 | Vriend | 600/538 |

FOREIGN PATENT DOCUMENTS

| | | |
|---|---|---|
| WO 97/32619 | 9/1997 | (WO) . |
| WO 97/50049 | 12/1997 | (WO) . |
| WO 98/41146 | 9/1998 | (WO) . |

OTHER PUBLICATIONS

Pennock, B.E., et al., *A Noninvasive Technique for Measurement of Changes in Specific Airway Resistance*, 1999 The American Physiological Society pp. 399–406.

Dorsch, W., et al., *Continuous Recording of Intrapulmonary "Compressed Air" as a Sensitive Noninvasive Method of Measuring Bronchial Obstruction in Guinea Pigs*, Pflugers Archiv, pp. 236–241.

Silbaugh, S.A., et al., *Noninvasive detection of airway constriction in awake guinea pigs*, The American Physiological Society pp. 1666–1669.

Gonzalez, H., *Accuracy of Respiratory Inductive Plethysmograph over Wide Range of Rib Cage and Abdominal Compartmental Contributions to Tidal Volume in Normal Subjects and in Patients with Chronic Obstructive Pulmonary Disease*, pp. 171–174.

Stick, Stephen, *Measurements During Tidal Breathing*, 1996 Wiley–Liss, Inc., pp. 117–138.

Adams, Jose Antonio, *Respiratory Inductive Plethysmography*, 1996 Wiley–Liss, Inc. pp. 139–164.

Adams, A., *Tidal Volume Measurements in Newborns Using Respiratory Inductive Plethysmography*, 1993 American Review of Respiratory Disease vol. 148, pp. 585–588.

\* cited by examiner

*Primary Examiner*—Robert L. Nasser
(74) *Attorney, Agent, or Firm*—Hamilton, Brook, Smith & Reynolds, P.C.

(57) ABSTRACT

The present invention relates to a system for measuring respiratory function of living organisms. More particularly, signals indicative of the effort, defined as active and passive work, required to breathe and the airflow through the respiratory system of the living organism are obtained and processed as waveforms to provide a signal indicative of the respiratory restriction. The methods of the present invention measure clinical forms of airway obstruction and airway reactivity and may be used to continuously or intermittently monitor patients with compromised respiratory function.

57 Claims, 39 Drawing Sheets

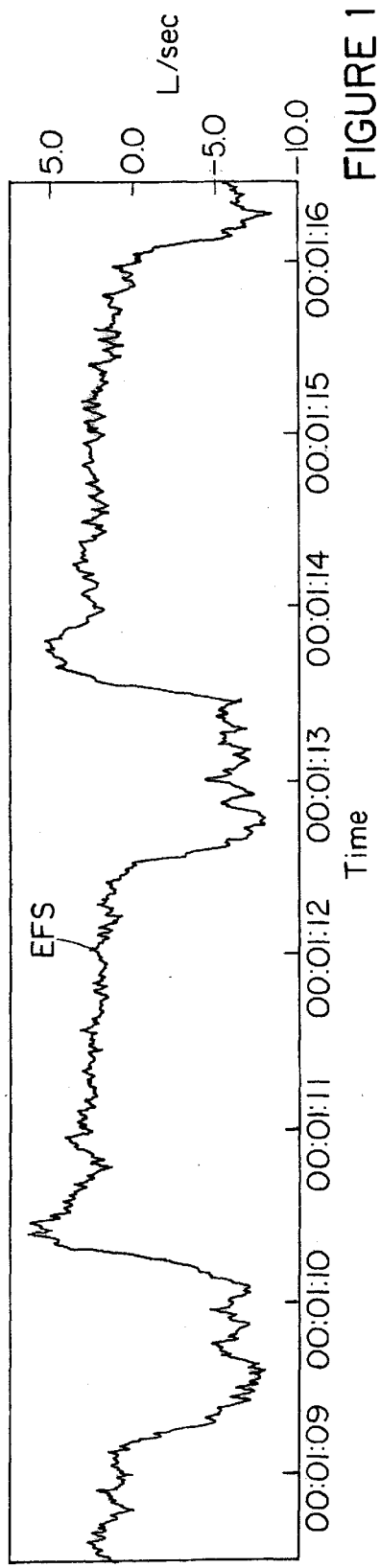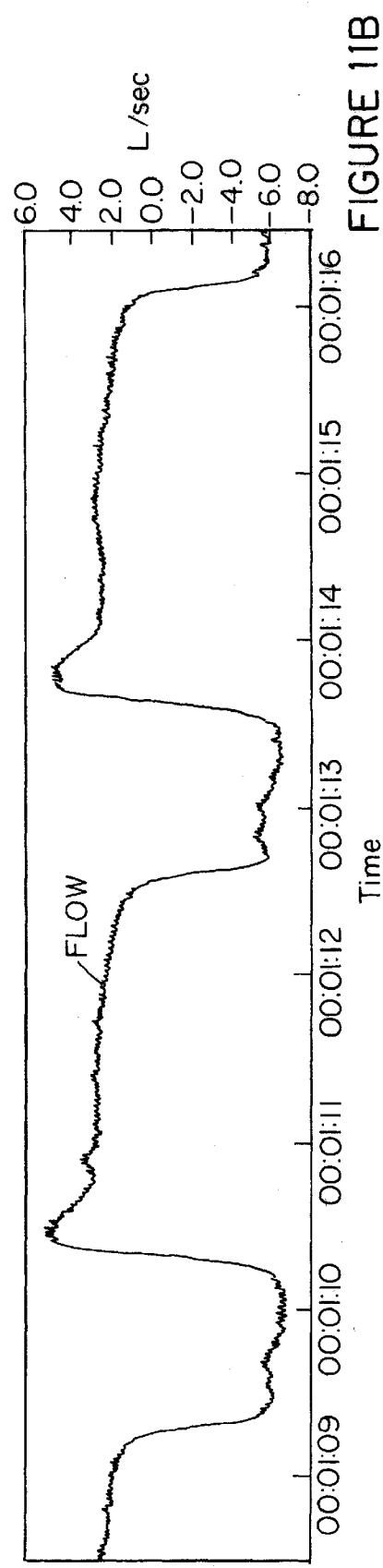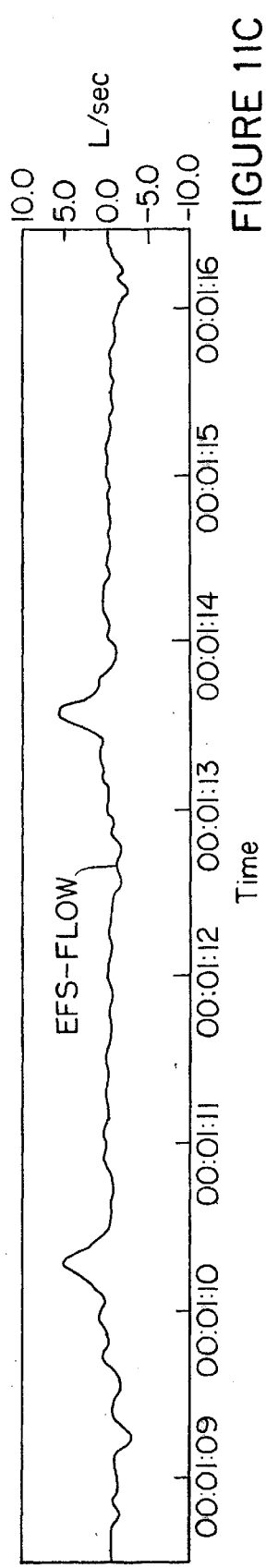
FIGURE 11A
FIGURE 11B
FIGURE 11C

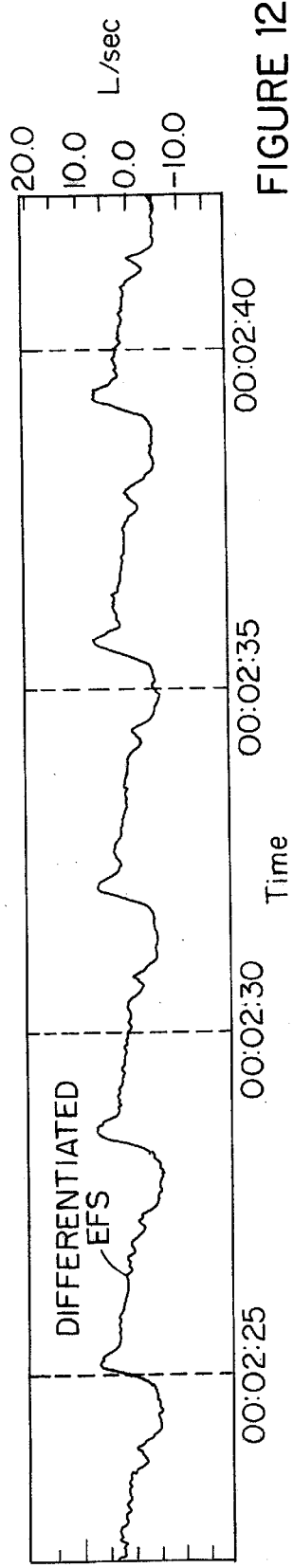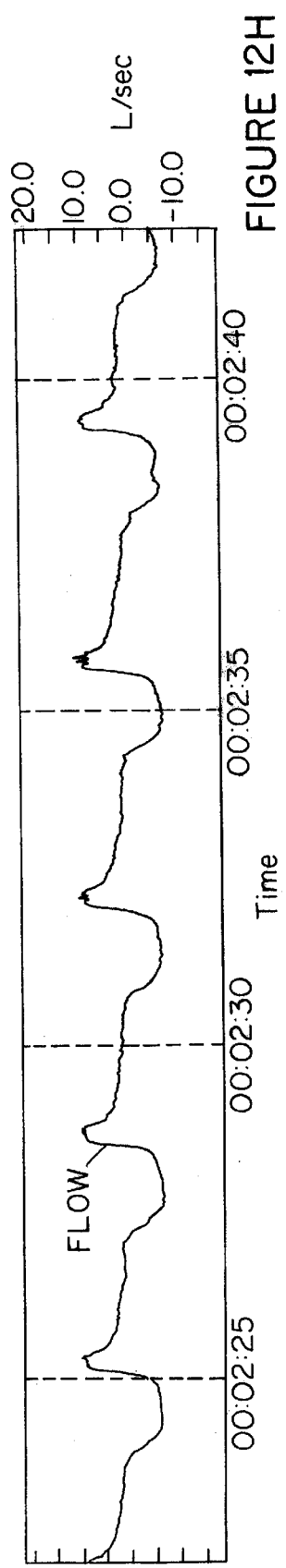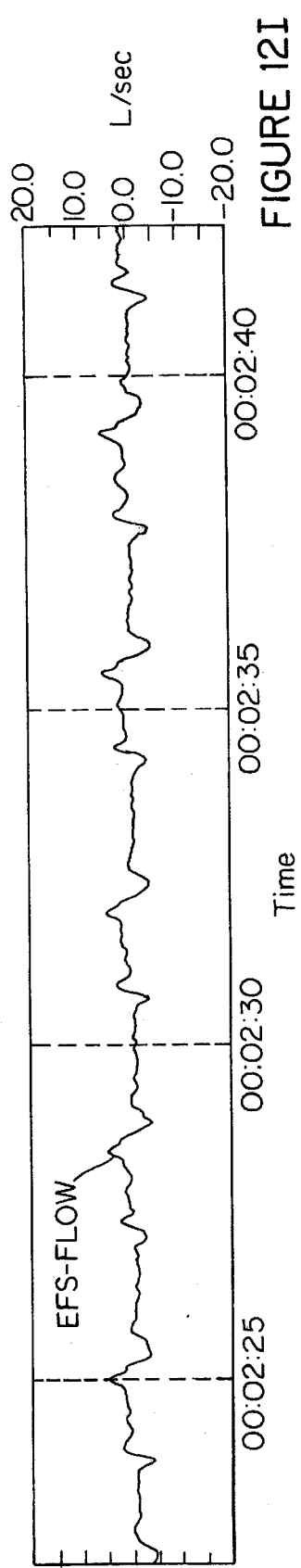
FIGURE 12G
FIGURE 12H
FIGURE 12I

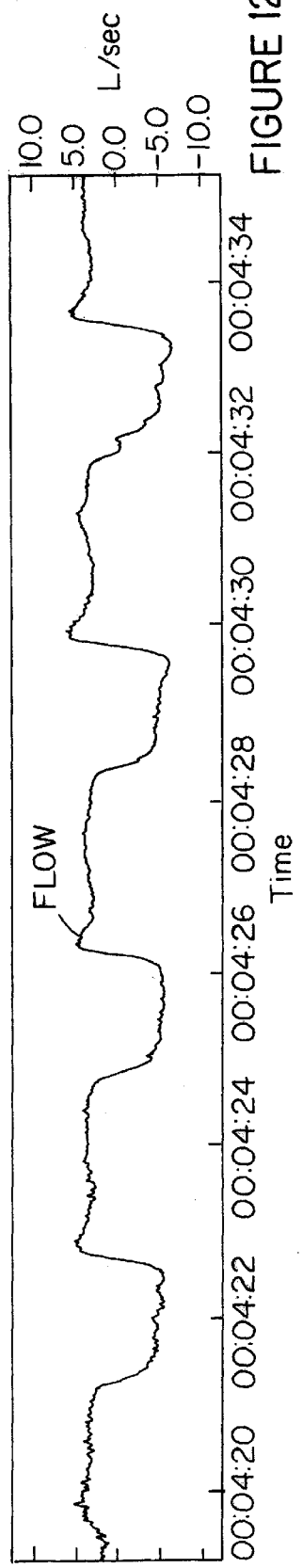
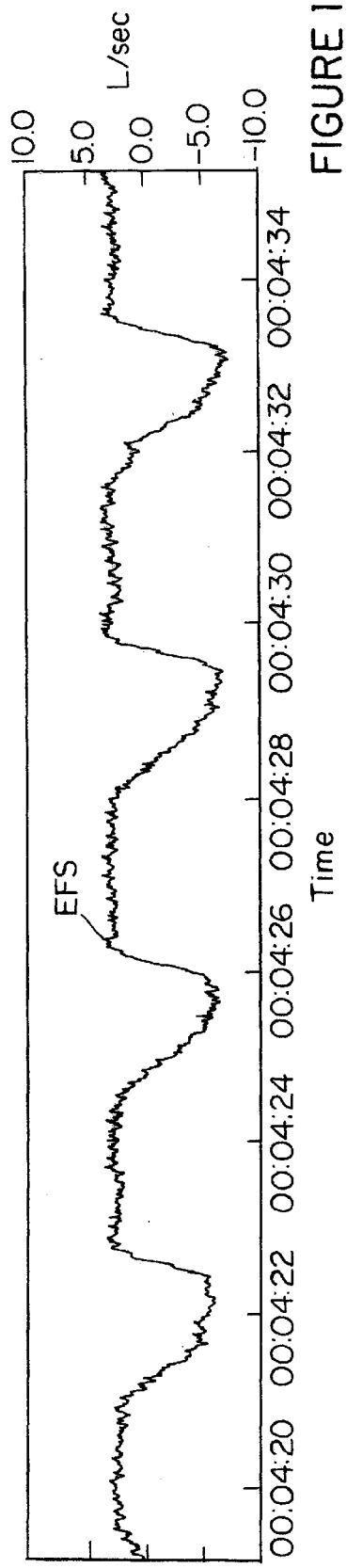
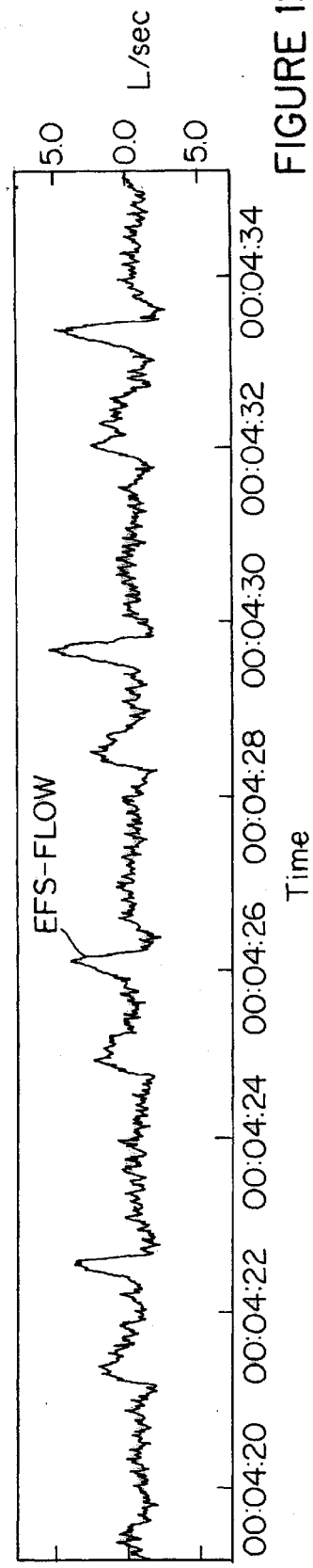
FIGURE 12N
FIGURE 12O
FIGURE 12P

| CLASSICAL MEASURE | EFS-FLOW |
|---|---|
| LOGPC65Cdyn | LOGPC135SFmax |
| 1.863 | 1.921 |
| 1.907 | 1.687 |
| 3.077 | 4.541 |
| 2.097 | 1.986 |
| 1.052 | 1.487 |
| 1.267 | 1.450 |
| 0.911 | 0.396 |

FIGURE 13G

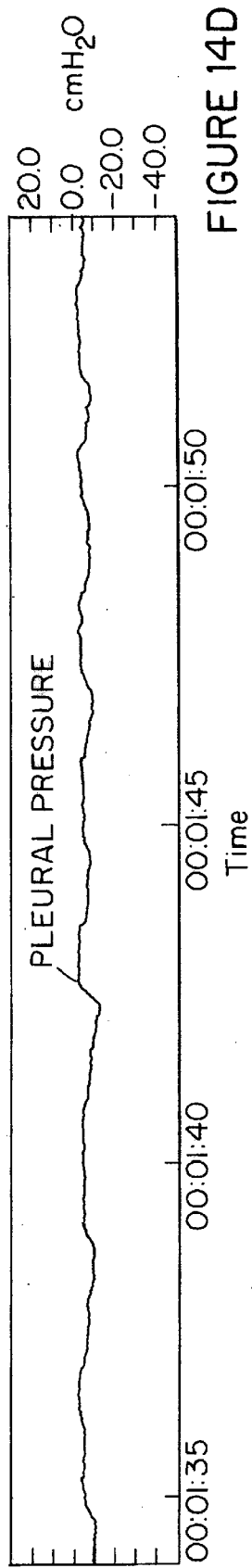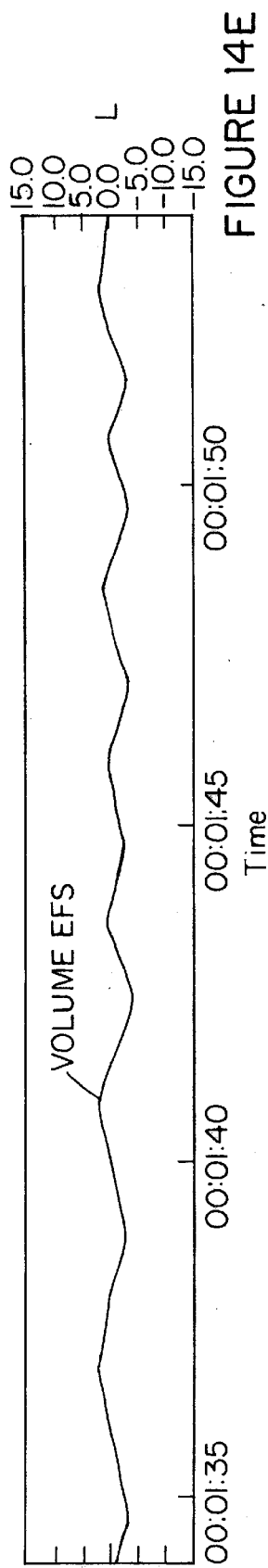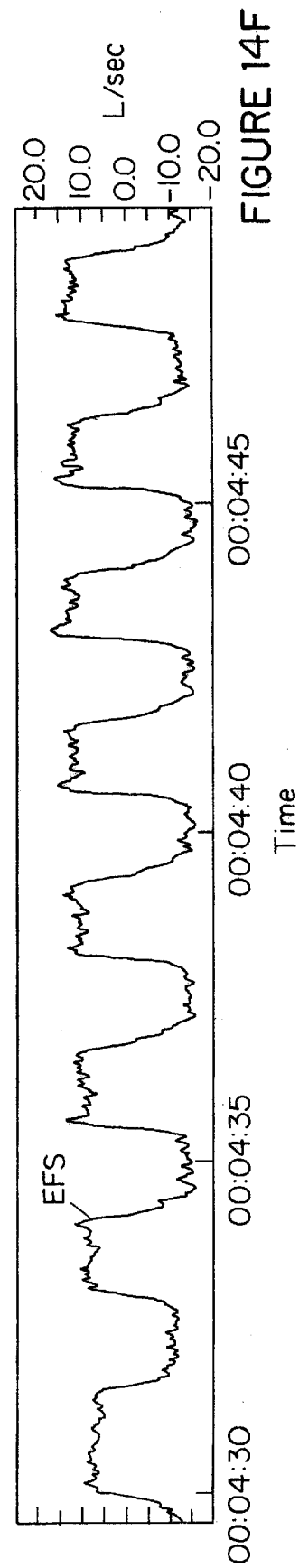

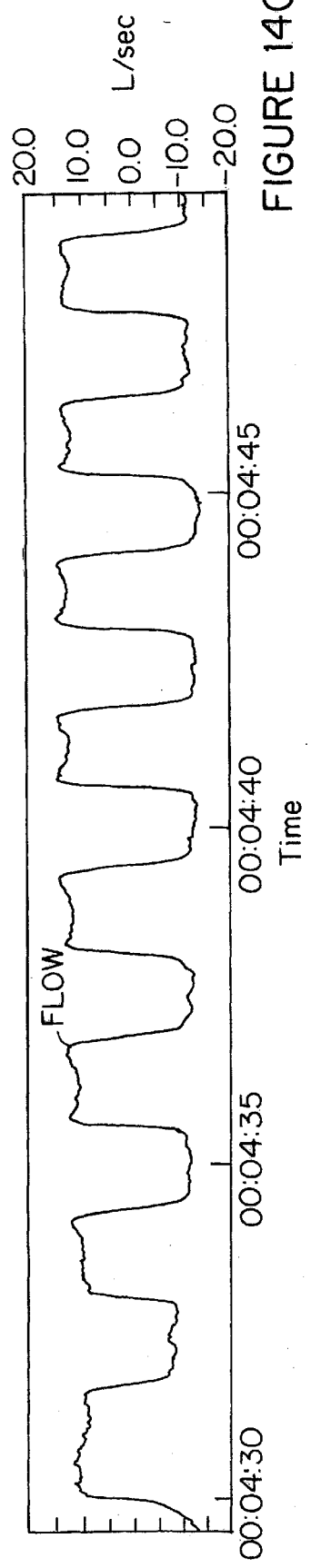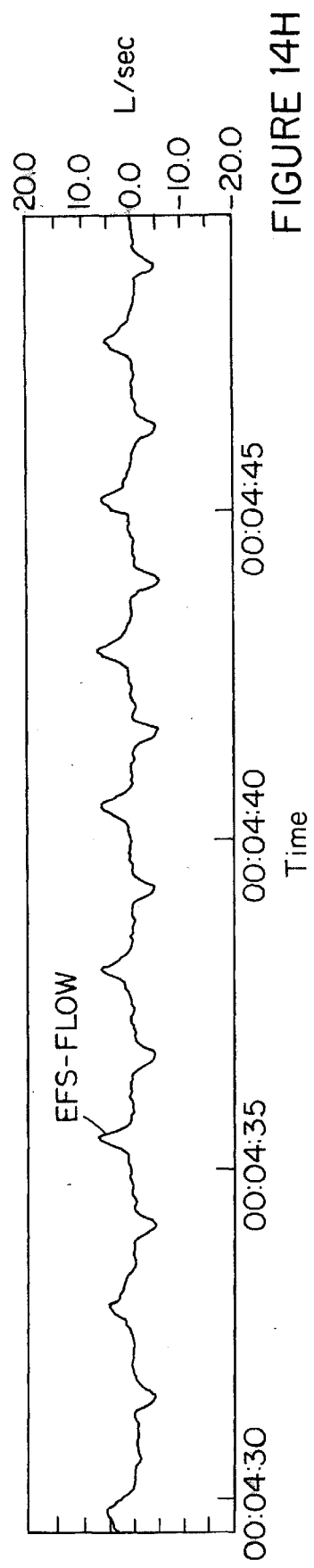

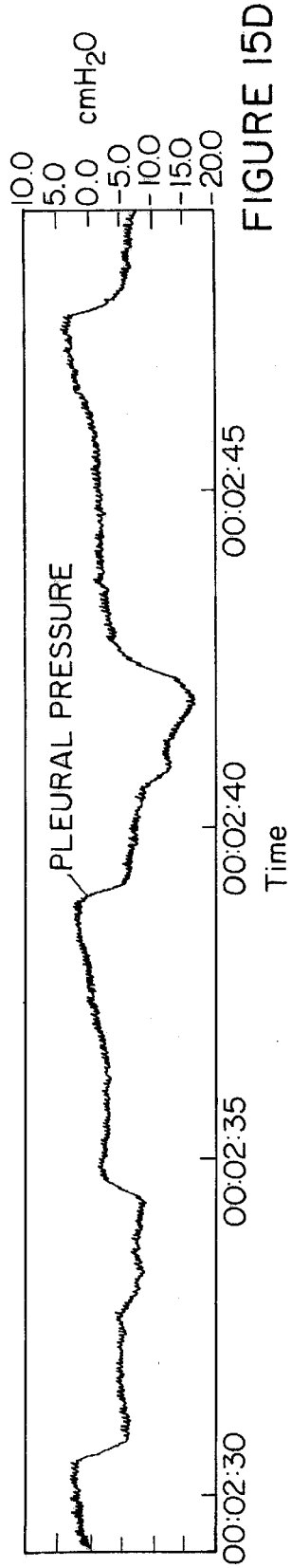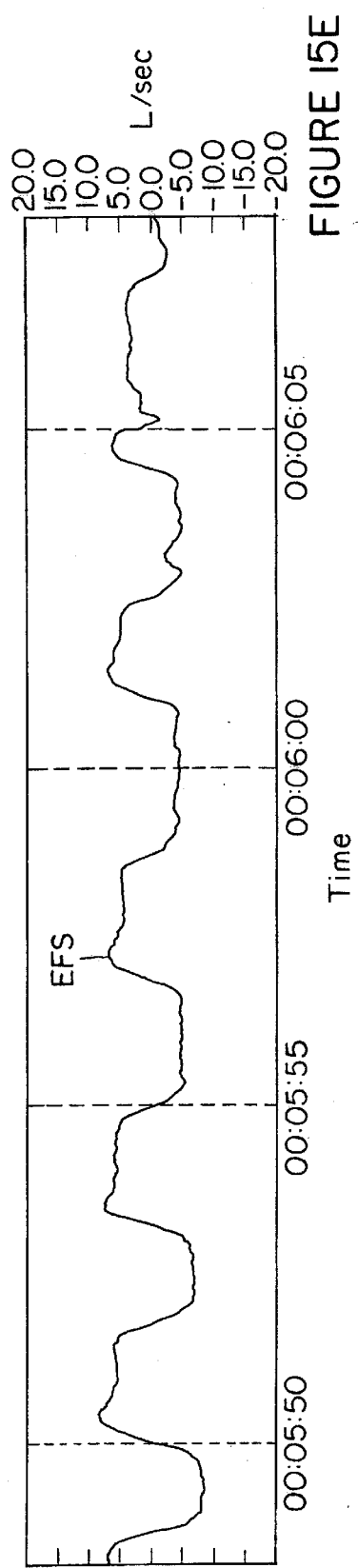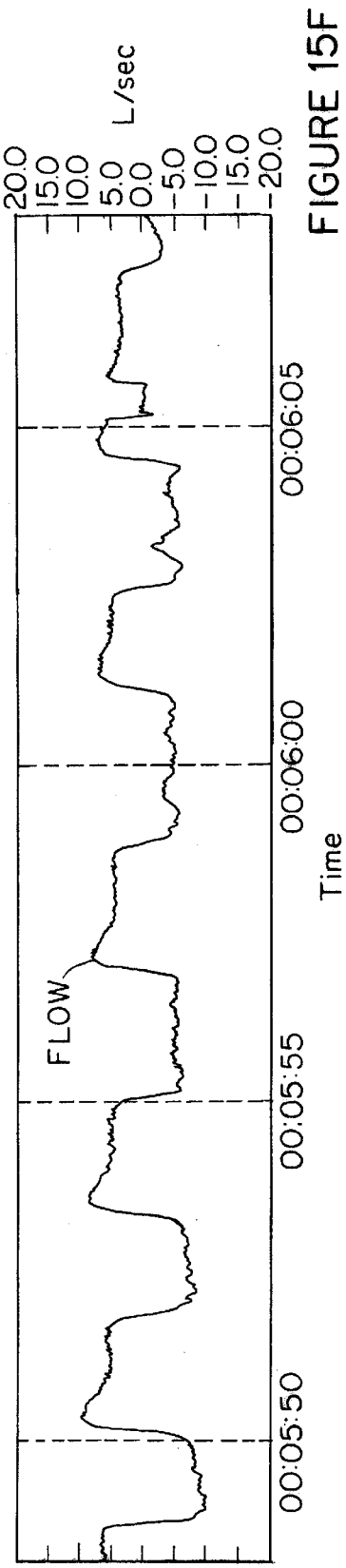

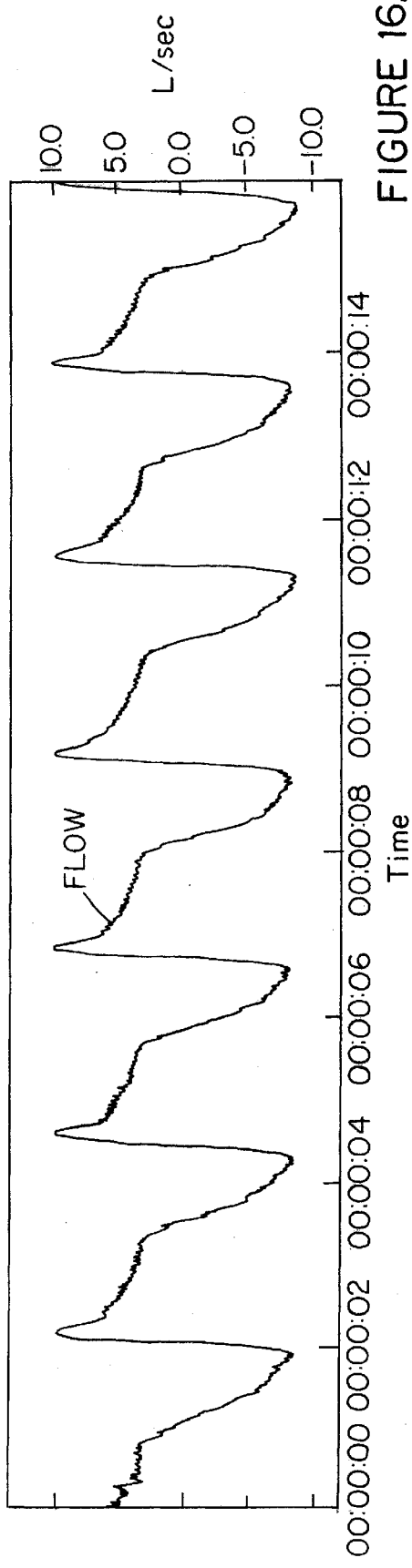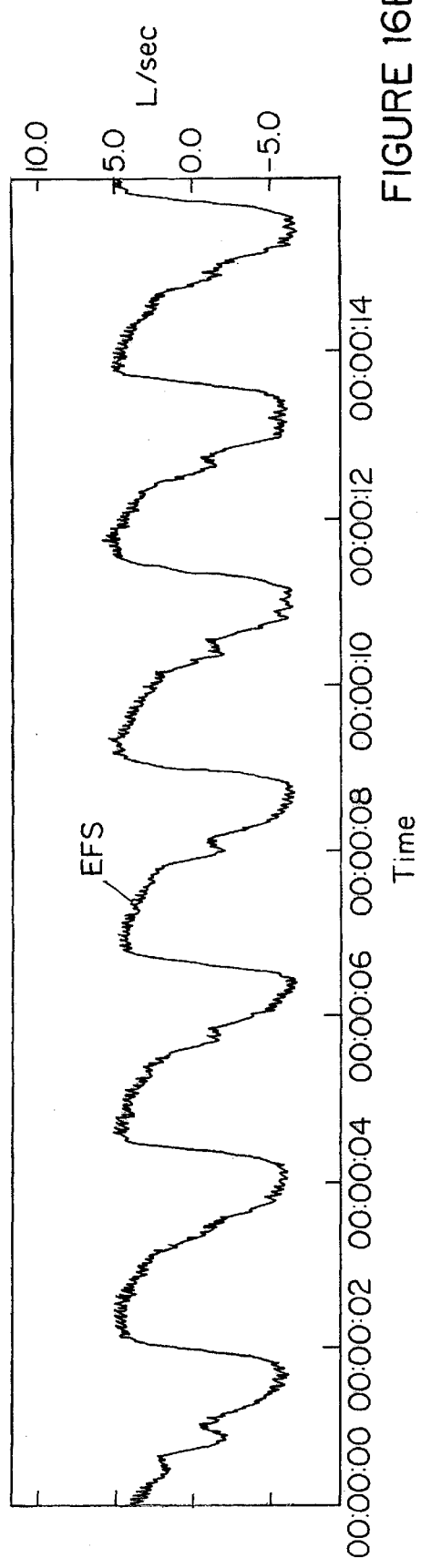

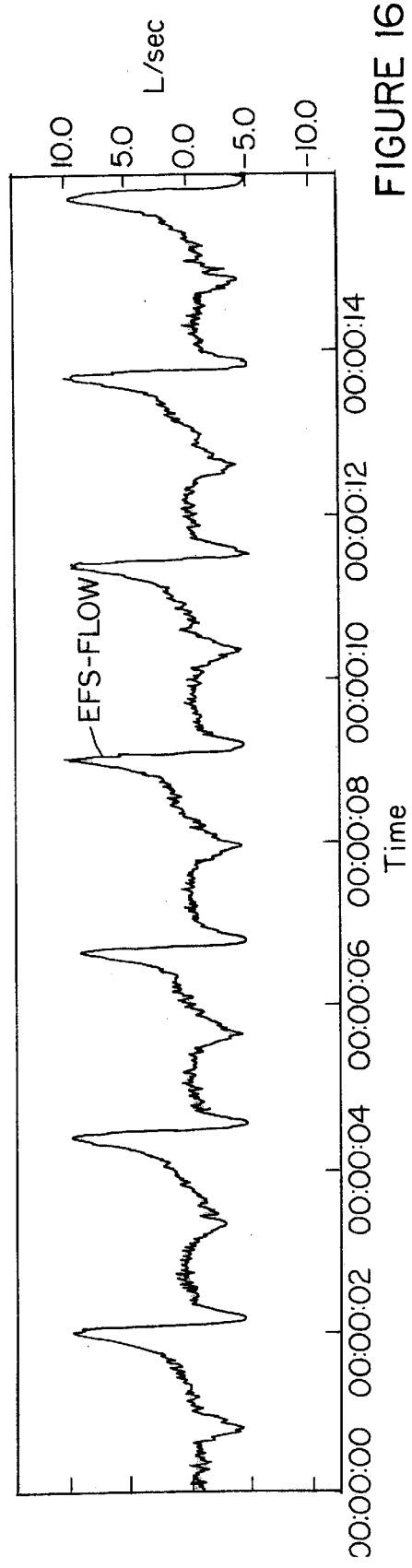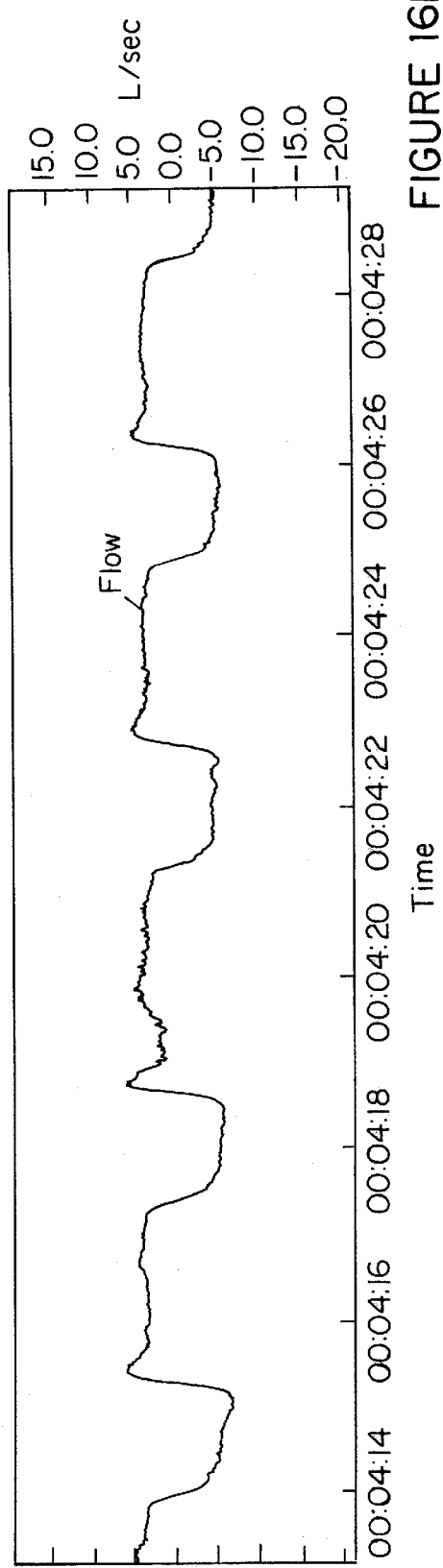

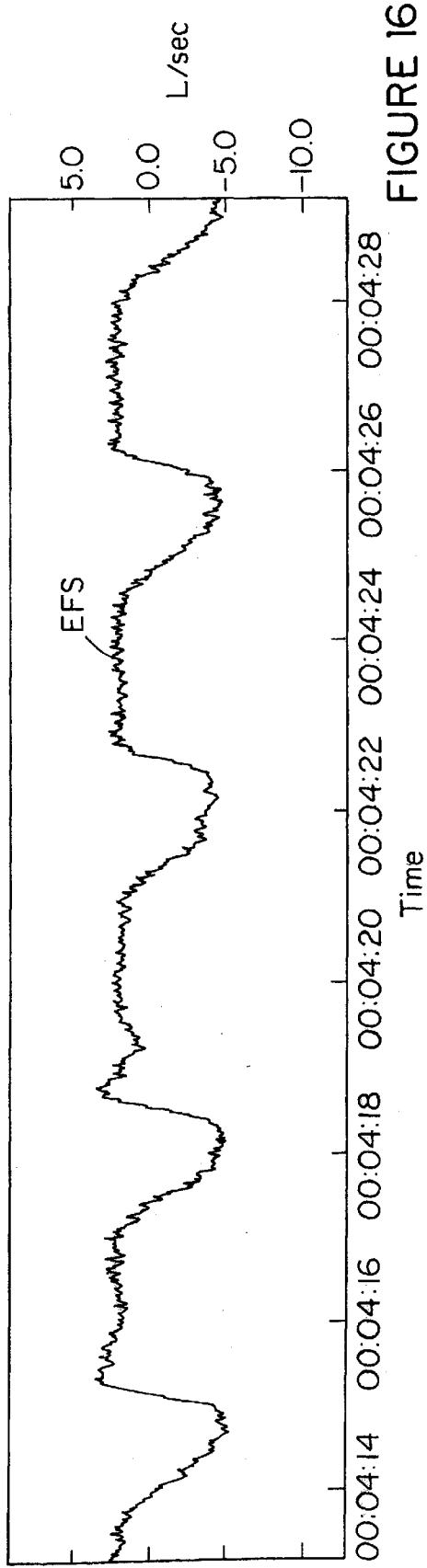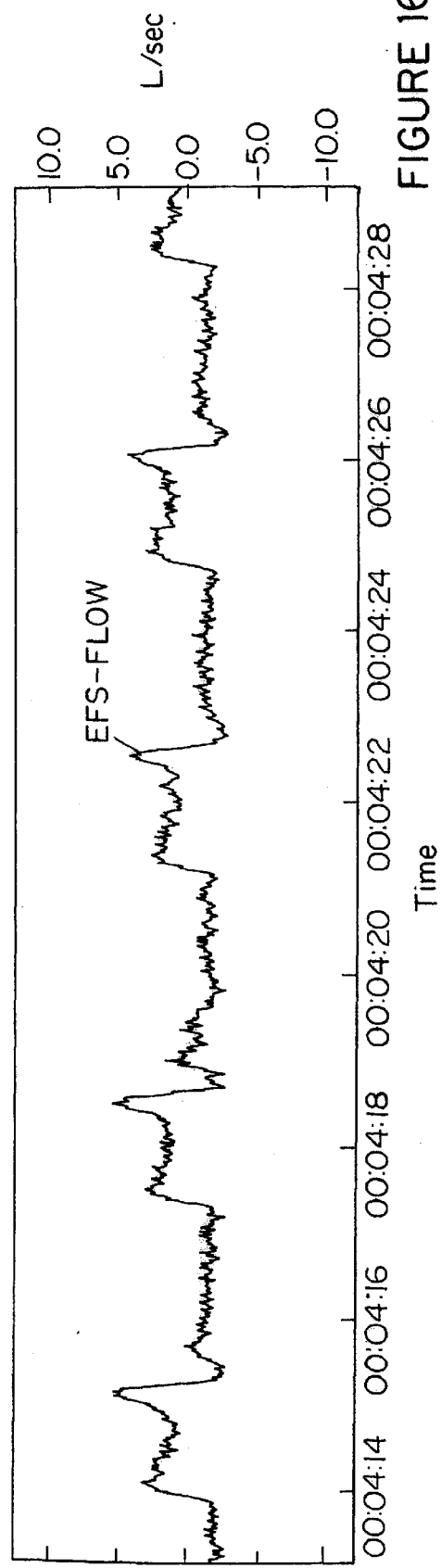

SYSTEM FOR MEASURING RESPIRATORY FUNCTION

BACKGROUND OF THE INVENTION

Information regarding respiratory function of a living organism is important in the field of medicine. Respiratory function provides a measure of how efficiently air is moved through the respiratory system, and thus provides important clinical information for the diagnosis and treatment of many respiratory conditions and diseases. Some examples of these conditions are chronic obstructive pulmonary disease (COPD), asthma, and emphysema. In addition, respiratory function measurements allow medical practitioners to observe effects of a bronchodilator or long-term treatments for COPD, or conversely, the airway responses to a bronchoconstrictor challenge for assessment of airway reactivity.

Respiratory function testing includes mechanical function tests which typically compare the effort or driving pressure put forth by the organisms to some quantifiable outcome, such as the output of flow or minute ventilation. Lung function tests differ based on how these inputs and outputs are assessed. Examples of inputs to the respiratory system that are measured, include diaphragmatic electromyographic activity, changes in thoracic esophageal pressure or pleural pressure, changes in airway pressures in ventilated subjects, or noninvasive measures of drive including respiratory inductance plethysmography or impedance plethysmography, and whole body plethysmography. Examples of output measurements include flow, tidal volume, or ventilation measurements using devices that collect flow at the airway opening. In general, the mechanical function of the respiratory system is best described by combining some measure of drive with output. Variables such as resistance and compliance can then be derived to assess the level of airway obstruction or loss of lung elasticity, respectively. This is the basis for classical physiologic modeling of the respiratory system: the comparison of transpulmonary pressure changes with flow or tidal volume, carefully assessed in the same time domain with avoidance of phase lag between signals.

Classical physiologic modeling measures total pulmonary resistance, dynamic compliance and related variables. However, the classical physiologic modeling relies on the invasive passage of an esophageal balloon for example, for measuring driving pressure, and flow as a measure of output. An esophageal balloon catheter is positioned in the midthoracic esophagus. Thus, classical physiologic measures are not used because of the invasive nature of the esophageal balloon catheter and the difficulty in calibrating the classical system under field conditions.

Lung function tests have evolved with respect to the sensors, recording devices, and analysis techniques used to evaluate input and output. However, a need still exists for the noninvasive determination of lung mechanical function and monitoring in human and animal subjects for clinical and research purposes. In this respect, a number of technologies to measure drive, mentioned above, are available. Devices such as single and double plethysmographs are used to measure drive. In the double chamber plethysmograph, thoracic and nasal flows are recorded as separate signals, whereas in barometric plethysmography, a single signal is recorded that is the net signal from the thoracic and nasal components. The latter is achieved simply on the basis that animals breathe inside a box where pressure changes are the net effects of both components. The aforementioned plethysmographic techniques, due to their size and complexity, preclude their use as a portable field test. In addition, these techniques enclose the subject, which is objectionable to both humans and animals.

A need still exists for improved systems and methods which provide for measuring respiratory function for health care practitioners, are portable and which are non-invasive to the living organisms.

SUMMARY OF THE INVENTION

The present invention relates to a system for measuring respiratory function of living organisms by measuring gas compression or expansion which is the difference between the effort (defined herein as having active and passive work components) required to breathe and airflow, by the combination of external sensors and direct measures of true flow. The system of the present invention uses a direct comparison of an external flow signal (EFS) indicative of effort required to breathe which includes both an active work component and a passive work component indicative of the passive recoil of the lung, diaphragm and chestwall during exhalation, and the uncompressed flow, preferably in the same time domain, thereby permitting real time analysis using a plurality of measured variables to assess respiratory function. The apparatus and methods of the present invention provide non-invasive measures of airway obstruction or respiration restriction in the subjects.

The present invention is important for patients/subjects with known clinical obstructions. Response to treatments such as bronchodilators can be monitored and assessed to measure improvements using the present invention.

In addition, it is important to measure respiratory function in subjects who have a subclinical form of an airway obstruction, i.e., the subjects who do not normally display the clinical symptoms associated with airway obstructions. The present invention provides diagnosis of subclinical progressive or episodic conditions by testing the airway reactivity of the subjects. This is accomplished by provoking an obstruction of the airways by challenging the airways with a chemical such as a histamine, for example, and using the present invention to measure changes in the respiratory function of the subject.

According to one aspect of the present invention, the methods for measuring respiratory function of the present invention include the steps of obtaining a signal indicative of the effort required to breathe by the living organism, obtaining a signal indicative of uncompressed airflow through the respiratory system of the subject as measured at the airway opening, processing the signals indicative of effort and flow by comparing the signals dynamically in the same time domain to detect transient periods of gas compression or expansion that signify airway obstruction and to provide a signal indicative of the respiration restriction of the subject. Increase in respiratory system impedance is therefore detected by measuring gas compression or expansion indirectly, using non-invasive sensors.

A preferred embodiment of the present invention to measure airway reactivity features obtaining a signal indicative of the effort required to breathe and also referred to herein as the external flow sensor (EFS), obtaining a signal indicative of airflow through the respiration system of the subject and processing the two signals which includes the comparison of the two signals to provide a signal indicative of the measure of respiration restriction of the subject. This method uses bronchoconstrictors to challenge the respiratory system of the subjects so as to provoke a response and test the airway reactivity of the subjects.

The preferred embodiment to measure airway reactivity may employ different sensors such as respiration induction plethysmography or impedance plethysmography or devices such as piezoelectric sensors to obtain the signal indicative of effort required to breathe. The signal indicative of uncompressed airflow through the respiratory system can be obtained through the use of a pneumotachographic measurement device, an ultrasonic device, a thermistor or a breath-sound intensity device. Additionally, the signal indicative of the effort required to breathe is calibrated by assigning a voltage span to the specific volume or flow span. Calibration for the signal indicative of uncompressed airflow is optional, but preferred in conjunction with the use of methods such as flow meters or precision volume syringes.

The signals indicative of the effort and airflow are amplified and digitized. The signals are then compared and subtracted to give an indication of the respiration function of the subject. A programmable computer can be programmed to perform an analysis of the measured signals and a display formatted to show the recorded and processed data. An electronic memory can be used to store the measured and/or processed data. The comparison of the effort or external flow signal with uncompressed airflowis performed either by overlapping the waveforms and performing visual comparisons between the two waveforms or by synthesizing a composite waveform by performing a digital subtraction point-by-point of the airflow from the external flow or effort signal. For a subject with a healthy respiration system, the effort and flow signals are in phase. However, during a condition such as one that occurs with bronchoconstriction, the airflow signal of the subject is no longer in phase with the signal indicative of effort or thoracic movement. During the condition when the airways are obstructed the effort signal or thoracic movement will lead nasal flow. This phase shift occurs in the time domain. The magnitude of the phase shift can be used as a measure of airway resistance or obstruction.

Another preferred embodiment of the present invention to measure clinical obstructions and response to treatments, such as the administration of bronchodilation medication, features obtaining a signal indicative of the effort required to breathe and a signal indicative of airflow through the respiration system and processing the two signals to obtain a signal indicative any respiration restriction of the subject. In another embodiment, the present invention can be used as a monitoring system for respiration functions. The advantage of the present invention in terms of its lack of obtrusiveness allows the subject to adopt normal body posture and yet be monitored. The monitoring application of the present invention is well suited for continuous or intermittent home or hospital monitoring of adults, children, infants and animal subjects. In particular, for patients on continuous positive airway pressure (CPAP) or assisted ventilation, the system of the present invention can be coupled to a CPAP delivery device or ventilator. The present invention triggers the use of the ventilators upon detecting respiratory restriction. Similarly, an oxygen delivery system can be coupled to the respiration function measurement system of the present invention.

According to another aspect of the present invention, an apparatus for obtaining a signal indicative of respiration of a living organism includes a first device that obtains a first input signal indicative of effort required to breathe by the organism, a second device that obtains a second input signal indicative of actual airflow through the respiratory system of the organism and a processing device that processes the first and second inputs to form a third signal indicative of respiration restriction of the organism. The processing device may be a programmable computer, programmed to perform an analysis of the measured input signals and a display formatted to show the recorded and processed data. The processing device can process the input signals using analog circuitry or digital circuitry. An electronic memory can be used to store the measured and/or processed data. The programmable computer can be a laptop computer, facilitating the portability of the apparatus. Thus, the system for measuring respiration function is lightweight and compact, having a weight of less than fifteen (15) pounds, preferably less than ten (10) pounds. This provides a portable system that can be readily transported by the user.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention. The principles and features of this invention may be employed in varied and numerous embodiments without departing from the scope of the invention.

BRIEF DESCRIPTION OF THE DRAWINGS

FIGS. 11A–11E graphically illustrate the effort, flow and comparative signals as measured and processed from an equine subject after administration of a bronchodilator.

FIGS. 12F–12J graphically illustrate the effort flow and comparative signals measured and processed from the equine subject used in FIGS. 12A–12E after administration of a bronchodilator.

FIGS. 12N–12P graphically illustrate calibrated and normalized flow, effort and comparative signals measured and processed from the equine subject used in FIGS. 12K–12M after administration of a bronchodilator.

FIG. 13G is a tabulation of a classical measure of airway resistance as compared with a measure of airway resistance provided by the method for measuring respiratory function in accordance with the present invention.

FIGS. 14A–14E graphically illustrate the effort, flow, comparative and pleural pressure signal of an equine subject without any airway obstructions.

FIGS. 14F–14J graphically illustrate the effort, flow, comparative and pleural pressure signals of the equine subject used in FIGS. 14A–14E during hyperventilation, in the form of hyperpnea.

FIGS. 15A–15D graphically illustrate the effort, flow, comparative and pleural pressure signals of an equine subject without any airway obstructions.

FIGS. 15E–15H graphically illustrate the effort, flow, comparative and pleural pressure signals of the equine subject used in FIGS. 15A–15D during hyperventilation, in the form of tachypnea.

FIGS. 16A–16C graphically illustrate the uncalibrated flow, effort and comparative signals from an equine subject having chronic obstructive pulmonary disease.

FIGS. 16D–16F graphically illustrate the uncalibrated flow, effort and comparative signals used in FIGS. 16A–16C after the administration of a bronchodilator.

DETAILED DESCRIPTION OF THE INVENTION

The present invention is directed to systems and methods for measuring respiratory function of subjects by measuring gas compression or expansion and airflow resistance by a combination of external flow sensors and direct measures of airflow. The external flow sensors measure effort required to breathe, which includes an active work component and a passive work component indicative of the passive recoil of the lung, diaphragm and chestwall during exhalation and are hereinafter referred to as effort or EFS signals or waveforms.

Figure 1:
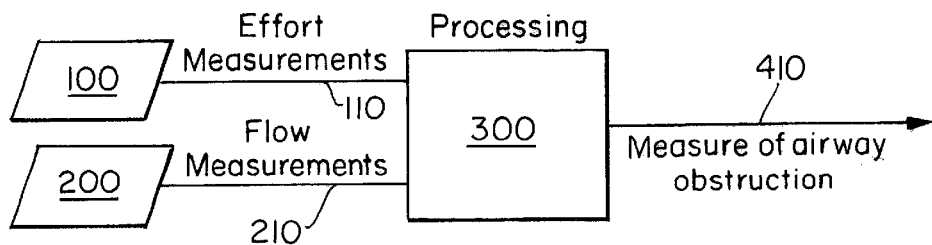
FIG. 1 is a top-level flow chart describing the method for measuring respiratory function in accordance with the present invention.

Referring to the drawings, FIG. 1 is a flow chart that describes the system for measuring respiration function in accordance with the present invention. Essentially signals 110 indicative of the effort required to breathe by a subject are obtained using an external flow sensor, along with signals 210 indicative of the uncompressed airflow in the respiratory system of the subject. The two signals are processed in processor 300 and a third signal 410 indicative of the difference between the effort and airflow signals is obtained which is a measure of airway obstruction, in the subject using the system of the present invention.

Figure 2:
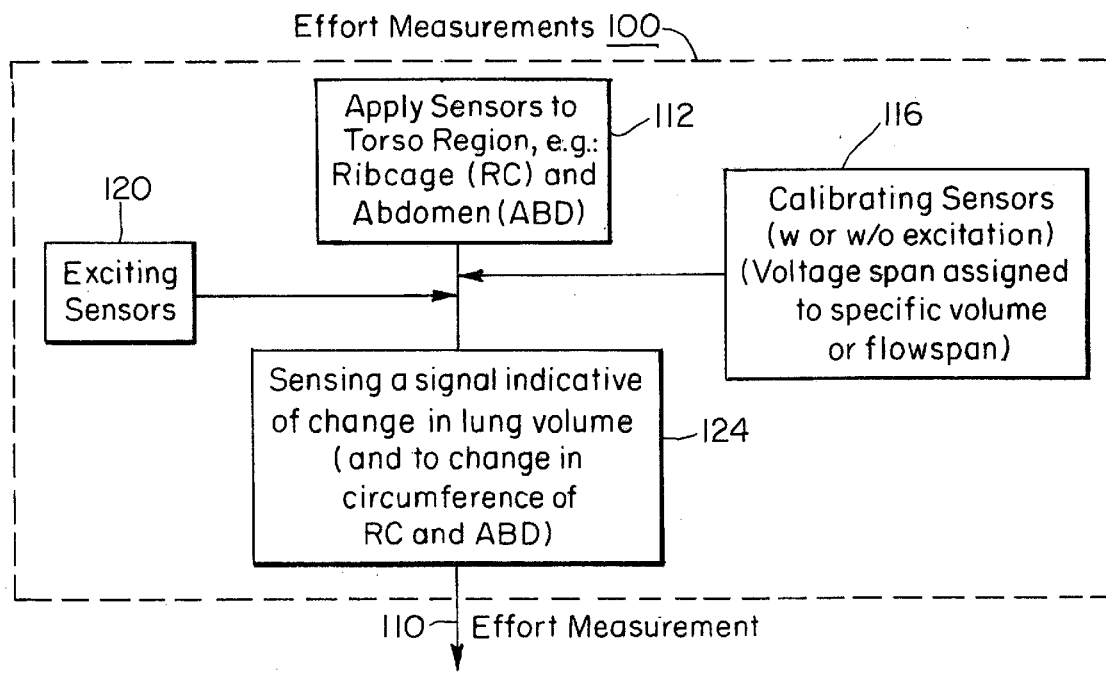
FIG. 2 is a flow chart describing the effort measurement methodology in accordance with the present invention.

Referring now to FIG. 2, the signals 110 indicative of the effort measurements are obtained by the step of applying external flow sensors 112 to the torso of a subject, for example to the rib cage and the abdominal regions of the subject. The sensors are calibrated per step 116 by exciting or alternatively not exciting the sensors. Essentially the voltage span is assigned to specific volume or flow spans. Once the signals are excited per step 120 after calibration 116, a signal indicative of the change in lung volume which is essentially a change in the circumference of the rib cage and the abdomen is collected per step 124 and obtained for further processing.

Figure 3:
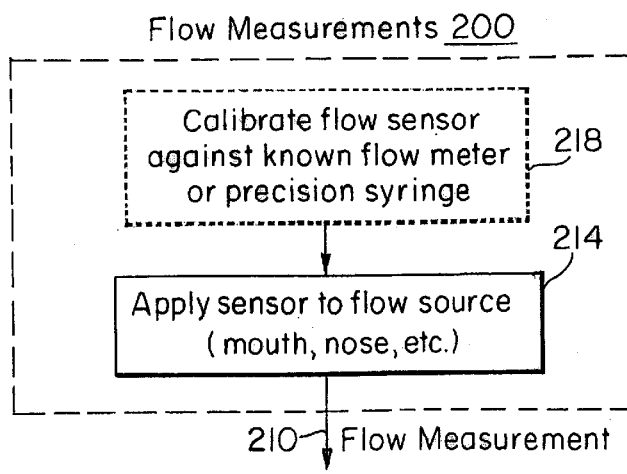
FIG. 3 is flow chart describing the airflow measurement methodology in accordance with the present invention.

Referring now to FIG. 3, airflow measurements are obtained, which are indicative of the uncompressed airflow through the respiratory system of the subject by the step of applying 214 sensors to the flow source, be it the mouth and/or the nose, etc. The calibration per step 218 of the flow sensor is not required for all measurements and is optional. However, if a calibration is performed it is done so by calibrating the flow sensor against a known flow meter or precision syringe. An uncalibrated flow sensor such as a sound microphone can be applied to gauge the airflow through the respiratory system.

Figure 4:
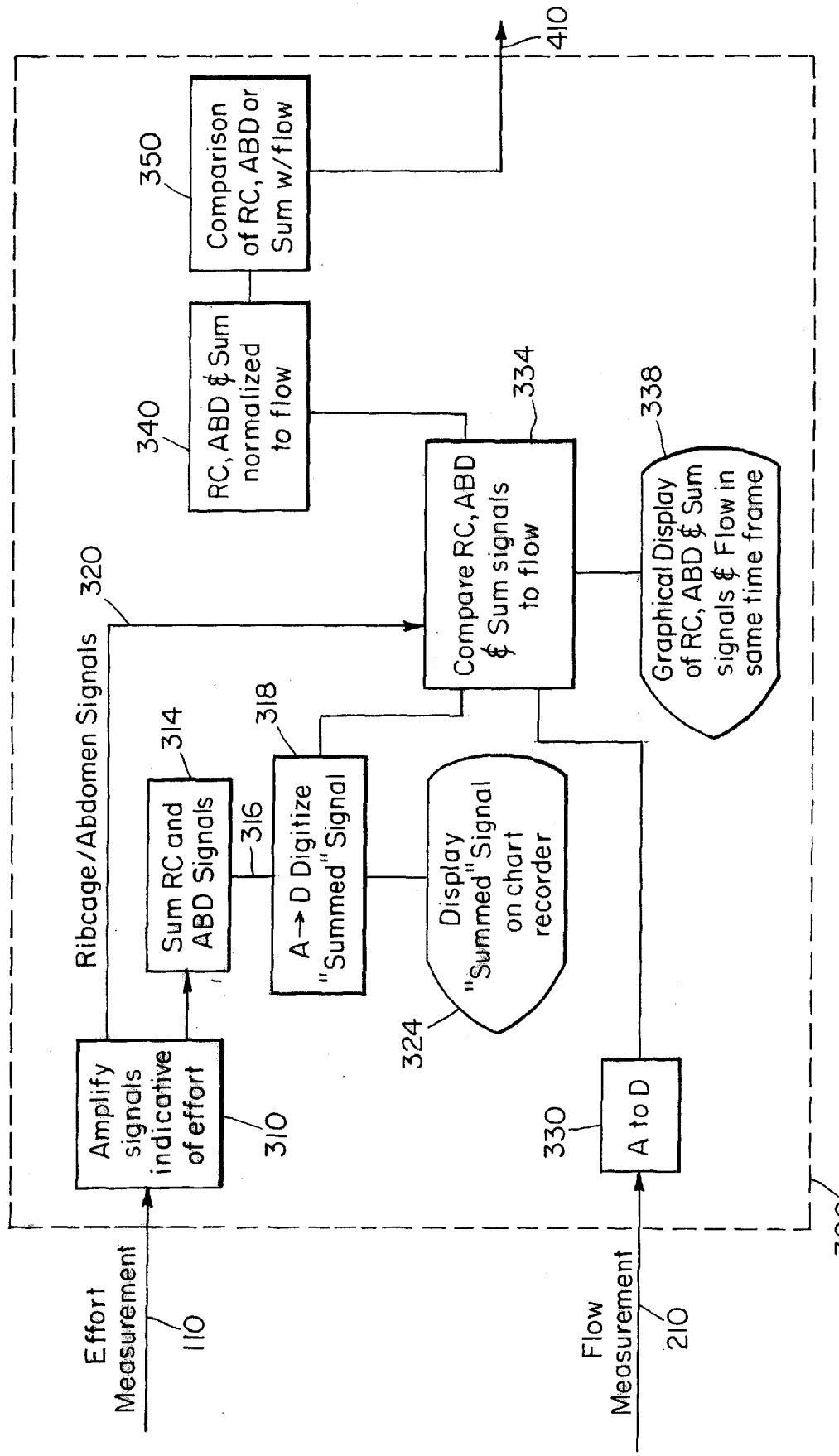
FIG. 4 is a flow chart describing the processing methodology in accordance with present invention.

Referring to FIG. 4, the effort measurements 110 and flow measurements 210 are then processed by the processor 300 of the present invention using a particular sequence of steps. The effort measurements are amplified per step 310. The rib cage and abdomen signals are summed per step 314 and the summed signal 316 is digitized per step 318. Alternatively, the analog signals can be used. The summed signal as well as the individual rib cage and abdominal signals 320 can be displayed on a chart recorder per step 324. The flow measurements 210 are also converted to digital signals per step 330. Both the effort measurements and airflow measurements, either as analog or digital signals, are then compared against each other per step 334 and the comparison can be graphically displayed in the same time domain per step 338. The rib cage, abdominal and summed signals are nonnalized to the airflow per step 340 prior to comparison of the signals. Normalizing preconditions the signals in order to provide a magnitude comparison. The inspiratory area of the airflow waveforms are used for normalization as the inspiratory area is typically not affected by lower airway obstructions. The comparison of the summed signal with airflow and the individual rib cage and abdominal signals with airflow is performed per step 350. Essentially, the airflow signals are subtracted from the effort signals using various algorithms. Effort and flow signals are compared dynamically, using digital point by point comparisons throughout each breath. As the frequency response of each sensor is matched, transient compression or expansion of gas due to obstruction is evident by instantaneous differences between effort and flow amplitude and phase. The resultant signal 410 of the comparison provides a measure of the respiratory function of the subject.

Figure 5:
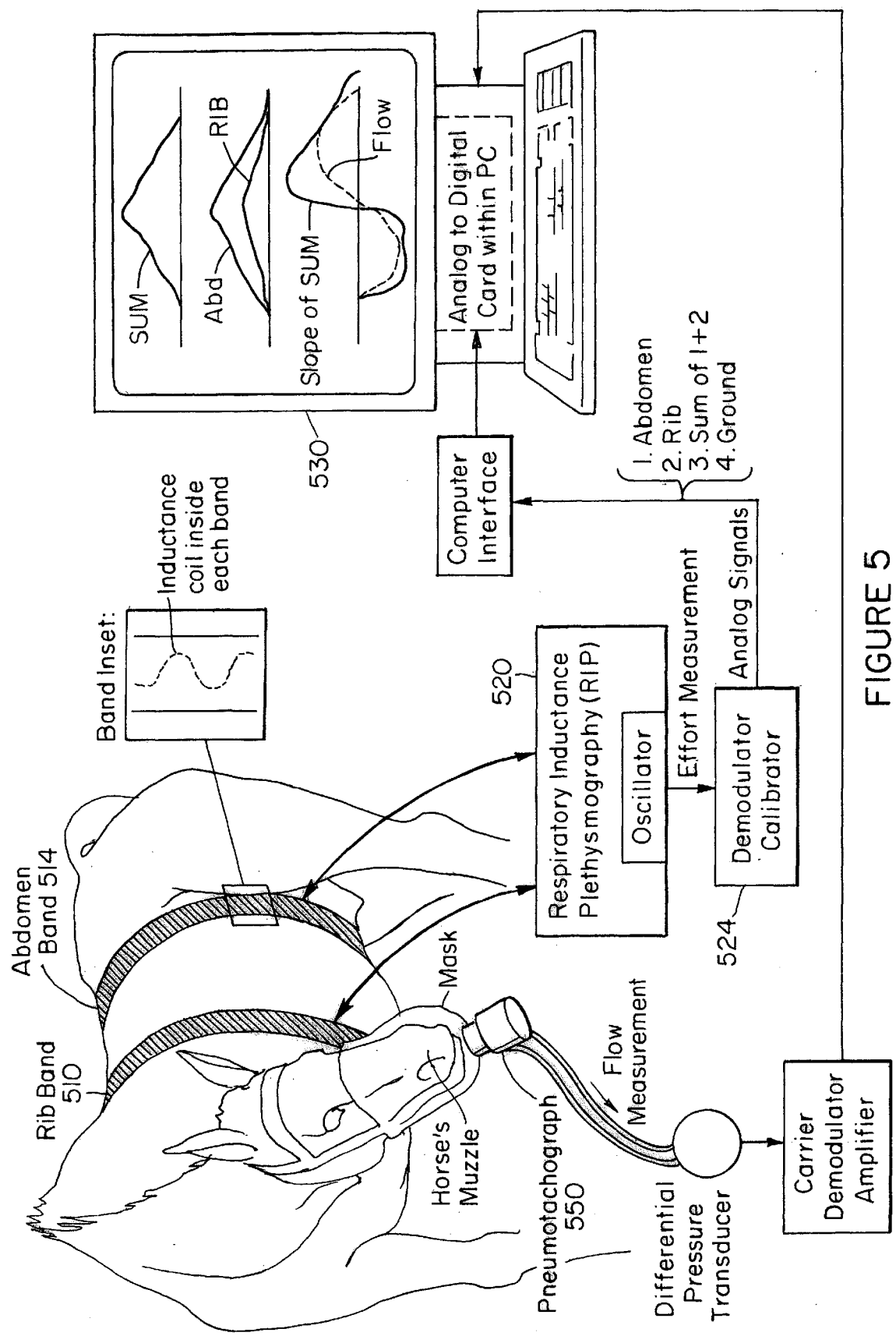
FIG. 5 is a schematic diagram of the system used for measuring respiratory function in horses in accordance with the present invention.

Referring to FIG. 5, the system to measure respiratory function uses respiratory inductance plethysmography (RIP)

which includes two self sticking elastic cloth bands placed around the rib-cage 510 and abdomen 514 to measure the effort or external flow. The bands can be folded unto themselves to create a snug fit. The bands contain a sinusoidal coil of wire sandwiched between two pieces of cloth band. The wire stretches with deflections of the subject's cross-sectional area of chest wall and abdomen with respiration. An external oscillator circuit 520 excites the wires with an oscillating voltage. Respiratory movements change the inductance of the coiled wires proportionally to the changes in volume of the rib-cage and abdomen. The change in inductance alters the net voltage across the coil. The voltage is demodulated and converted into an analog signal per step 524 that can be amplified and recorded by computer software on a real time basis, and replayed for post-acquisition analysis. Alternatively, the use of a piezoelectric sensor and amplifier to measure effort directly provides a flow signal, thus, not requiring differentiation of a volume signal which typically adds noise and may potentially change the characteristics of the effort signals, i.e., either the magnitude or phase components.

Voltage recordings of RIP are converted by software in a processor 530 into differentiated waveform of the volume deflections of the sum of the rib and abdomen bands if necessary. The difference in magnitude between the differentiated sum and flow waveform peaks or areas of particular segments of the breath are calculated. RIP has been used in human medicine to measure tidal volume and respiratory frequency and to detect apnea in adults, infants, and children. The system can also be used to monitor breathing patterns. RIP is based on the similar concepts of barometric plethysmography and is therefore confounded by similar factors. In barometric plethysmography, for instance, thoracic movement overestimates flow in patients with airway obstruction because of gas compression. The degree that thoracic movement overestimates flow can be used as a quantitative measure of obstruction. More recently, non-invasive whole body plethysmography or single chamber barometric plethysmographyhas been used in this regard. This technique is based on the fact that an animal in a closed chamber creates pressure fluctuations within the chamber with respiration. With inspiration, air is moved from the chamber into the animal, and the pressure within the chamber decreases. The air is warmed and humidified within the animal and thus the air expands as does chest volume. This thoracic flow increases the pressure measured in the chamber to a greater extent than the drop in pressure caused by nasal flow. The pressure in the chamber, or box pressure, reflects the net differences of these two processes. Tidal volume can be determined from these pressure changes in normal subjects.

During bronchoconstriction or other obstructive disorders, air is compressed in the animal. Nasal airflow of the animal is no longer in phase with thoracic movement. Thoracic movement leads nasal flow. This phase shift affects the box pressure signal in the time domain. The magnitude of the phase shift can be used as a measure of airway resistance. The degree of bronchoconstriction can be quantified by analyzing the shape of the waveform.

The same concept of gas compression with bronchoconstriction and phase delay can be detected by the RIP system when compared with flow. This technique of non-invasive monitoring of respiration is based on the separate contributions of rib-cage and abdomen to tidal volume. The respiratory system can be approximated by two degrees of motion, displacements of the rib and abdomen compartments then compared to flow on the same time scale.

The lung function testing methodology of the present invention combines a pneumotachograph 550 or other flow sensors for flow measurement with RIP bands or other external sensors. Just as there is a measurable change in the magnitude and phase of nasal versus thoracoabdominal signals in a box plethysmograph, similar changes are detected by measuring RIP and flow separately. This methodology enables medical practitioners to evaluate the response of humans or animals such as horses with chronic obstructive pulmonary disease (COPD) to bronchodilators, and to monitor the progression of the disorder.

Calibration of Respitrace ® bands or other sensors which are used as the RIP bands or sensors in human medicine can be performed using the iso-volume method which relies on training the patient to shift a held breath between the abdominal and rib compartments of the respiratory system. Another method, the least mean squares regression technique relies on varying body position or by taking measurements in different sleep stages and solving simultaneous equation. Both these methods are not appropriate for equines.

A possible method of calibration in horse is the qualitative diagnostic calibration method. This method does not require active subject cooperation as it is carried out during a five minute period of natural breathing in one posture. A proportionality constant of the relative contribution of rib and abdomen can be determined and applied to the system.

The types of flow sensors that may be used for practicing the present invention includes pneumotachographs. Two types of pneumotachographs that may be used are a Fleisch type and a screen-resistor type such as one supplied by Hans Rudolph, Inc. The pneumotachograph such as the one supplied by Hans Rudolph uses a unique housing configuration and screen assembly design to convert the flow of gas into a proportional linear signal of differential pressure from the two pressure taps for input into a differential gas pressure transducer. Another kind of flow sensor which may be used is an ultrasonic flow sensor which also provides a linear signal. In addition, thermistors such as a hot-wire anemometer may be used to measure flow. Further, a breath sound intensity flow sensor may also be used to gauge flow.

Effort sensors may comprise respiratory inductance plethysmography, such as sensors supplied by Sensor Medics, Inc., or Ambulatory Monitoring, Inc. The functions of oscillation and demodulation for RIP bands may be provided by a personal computer interface box. In addition, piezoelectric sensors which are excited with stretching or bending may also be used to provide a signal indicative of effort with the advantage of providing a flow signal directly. No differentiation of the measured signal is required as the measured signal is the flow signal unlike the RIP bands which measures a volume change.Impedance plethysmography may also be used to provide a signal indicative of the effort.

Figure 6A:
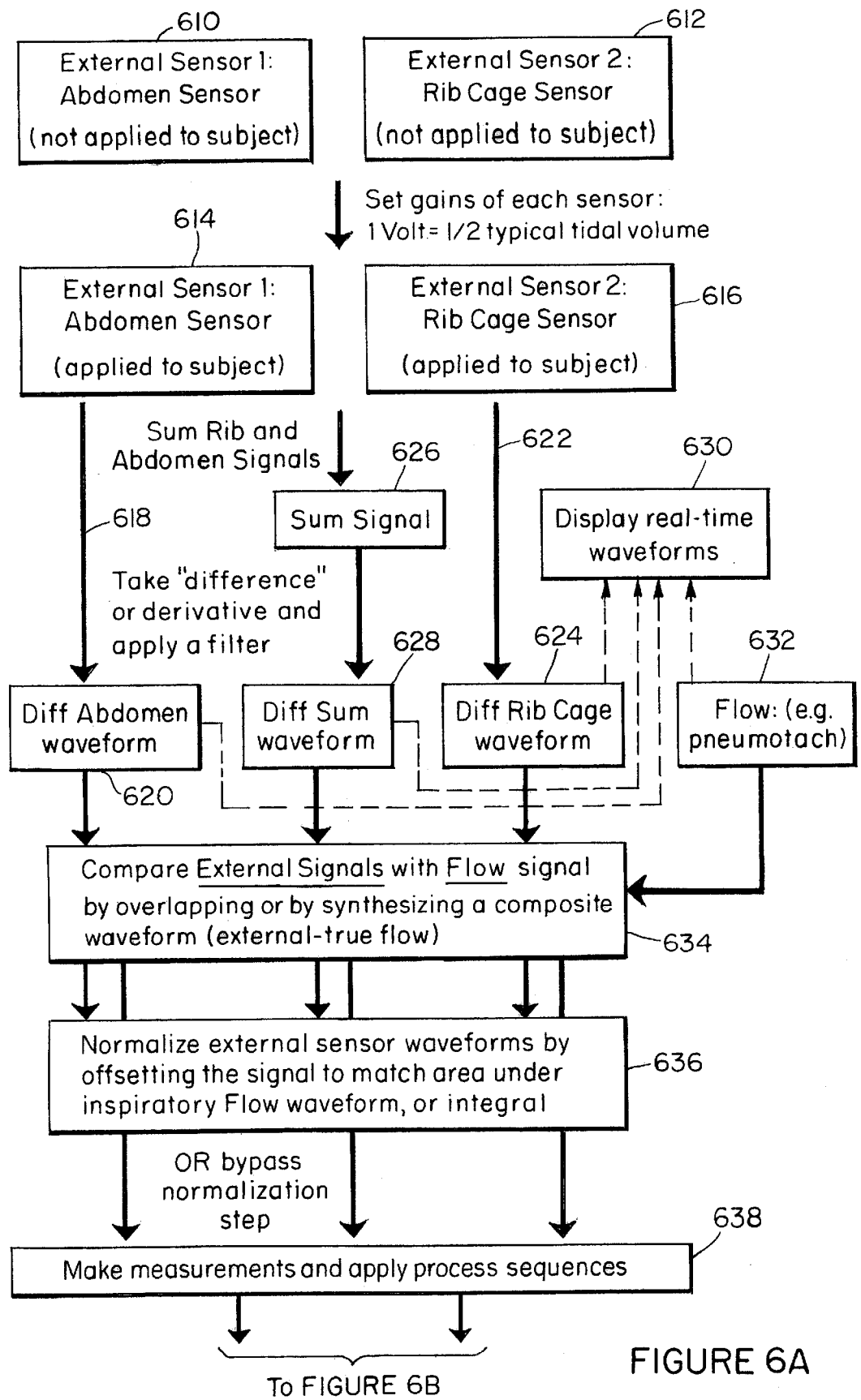
FIGS. 6A and 6B are flow charts describing the details regarding the processing of the signals measured in accordance with the present invention.
Figure 6B:
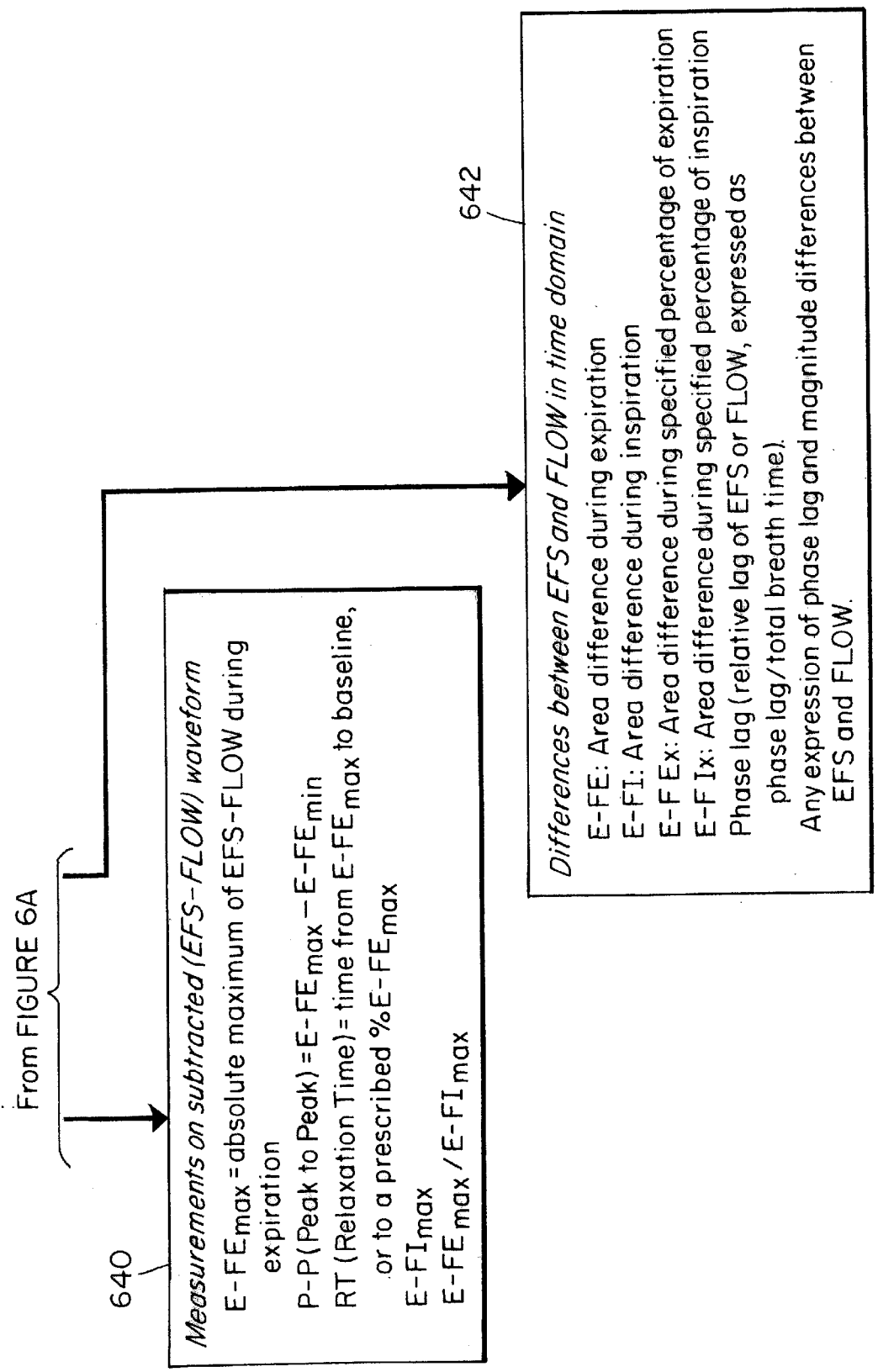

Referring to FIGS. 6A and 6B two external sensors, one for the abdomen 610 and another for the rib cage 612 are calibrated. The gains of each sensor are set to correspond to a pre-selected tidal volume. The external sensors, both for the abdomen and the rib cage, are then applied onto the subject at the respective locations 614, 616. The abdominal sensor results in a signal 618 which is the effort or external flow signal indicative of volume changes measured in the abdominal region. This abdominal waveform is differentiated per step 620. The rib cage sensor results in a signal 622 which is differentiated to result in the differentiated waveform indicative of the external flow signal per step 620. In addition, the two signals originating from the rib cage and the abdomen are summed in the summer 626 and the derivative of the two signals is then taken to result in a differentiated sum waveform 628. The three differentiated signals or waveforms 620, 624, 628, resulting from the abdomen, the rib cage and the summed signal, are displayed real time 632 and compared with the flow signal 632 either by visually displaying and overlapping the waveforms or by synthesizing a composite waveform per step 634 indicative of the point-by-point subtraction of the flow signal from the effort signal. The external effort signals or waveforms are normalized per step 636 by offsetting the signal to match an area under the inspiratory flow waveform. The step of normalization 636 is optional. The signals that result from the comparison of the external effort signal and flow signal are then processed by applying a process sequence per step 638. The measurements applied to the composite waveform resulting from subtracting the flow from the effort signal or external flow signal (EFS) are provided in step 640. One process sequence comprises subtracting the maximum flow during expiration from the absolute maximum effort signal. Other processes which can be applied comprise peak-to-trough measurements of the subtracted waveforms during expiration. An alternative measurement of the composite waveform (EFS-Flow) comprises calculating a relaxation time signal which is indicative of the time from the peak composite signal to the trough during expiration or from the peak to a prescribed percentage of the peak composite signal during expiration. Other measurement processes comprise subtracting the maximum inspiratory flow from the effort signal or a ratio of the maximum flow during expiration subtracted from the effort signal to the maximum flow during inspiration subtracted from the effort signal.

Other methods for comparing the overlapping signals indicative of effort and flow in the time domain are provided in step 642. One such method comprises measuring the area difference during expiration, or measuring the area difference during inspiration. Alternatively, the area difference during a specified percentage of expiration or inspiration can also serve to highlight the difference between the effort and the flow signals in the time domain. Alternatively, the relative phase lag between the effort or the flow signals expressed as a ratio of phase lag to the total breath time could also provide the difference between the two signals. Thus, generally any expression of phase lag and magnitude difference between the effort and flow signals provide the measures for the overlapped comparison signal.

Figure 6C:
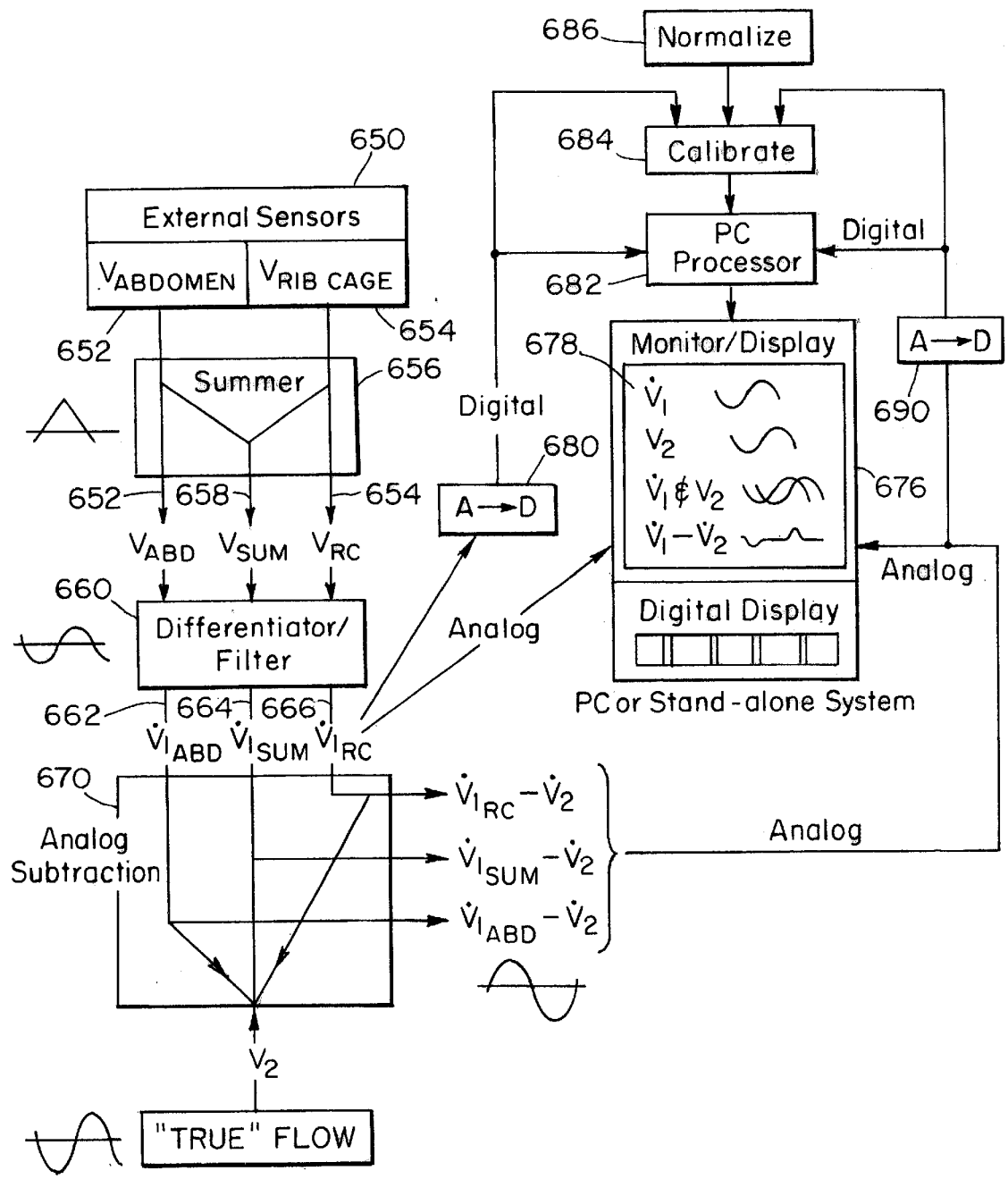
FIG. 6C is a schematic diagram of the hardware components required to implement the method for measuring respiratory function in accordance with the present invention.

Referring to FIG. 6C, a schematic diagram of the hardware components required to implement the system for measuring the respiratory function in accordance with the present invention is illustrated. External sensors 650 to measure effort, both from the abdominal and rib cage region, are applied to the subject and signals indicative of the effort required both from the abdominal region 652 and the rib cage region 654 are collected and summed in summer 656. The resultant signals, $V_{sum}$ 658, $V_{rc}$ 654 and $V_{abdomen}$ 652 provide input into a differentiator and filter 660. The signals as measured from the subject are indicative of a volume change during breathing and are differentiated to result in a flow signal represented by Vdot. Filtering of the differentiated signal is required to filter noise components added by the process of differentiation. The resultant signals $Vdot_{abdomen}$ 662, $Vdot_{sum}$ 664 and $Vdot_{rc}$ 666 form the inputs into an analog subtraction device 670. True flow 672 as measured by the pneumotachograph, is subtracted out from the differentiated signals resulting in the difference between the effort signals as represented by the signal for the rib cage, the abdomen and the sum, and the true flow signal. The analog signals then form inputs into a processing system 676 and are displayed on a monitor or a display 678. In the alternative, the signals that result from the analog subtractor 670 are digitized in an analog to digital converter 680 providing input into a processor 682. The output of the processor 682 is then displayed on a monitor 678. Calibration information 684 provides an input into the processor 682 which is used to normalize the effort signal per step 686 to an inspiratory area for example, or any other parameter to provide for magnitude comparisons of the effort and flow signals. In the alternative, the analog signals that result from the analog subtractor 670 can be displayed using the monitor 678. An analog to digital converter 690 can then convert the analog signals resulting from the analog subtractor 670. The digitized signals provide inputs into the processor 682 for further processing.

Figure 6D:
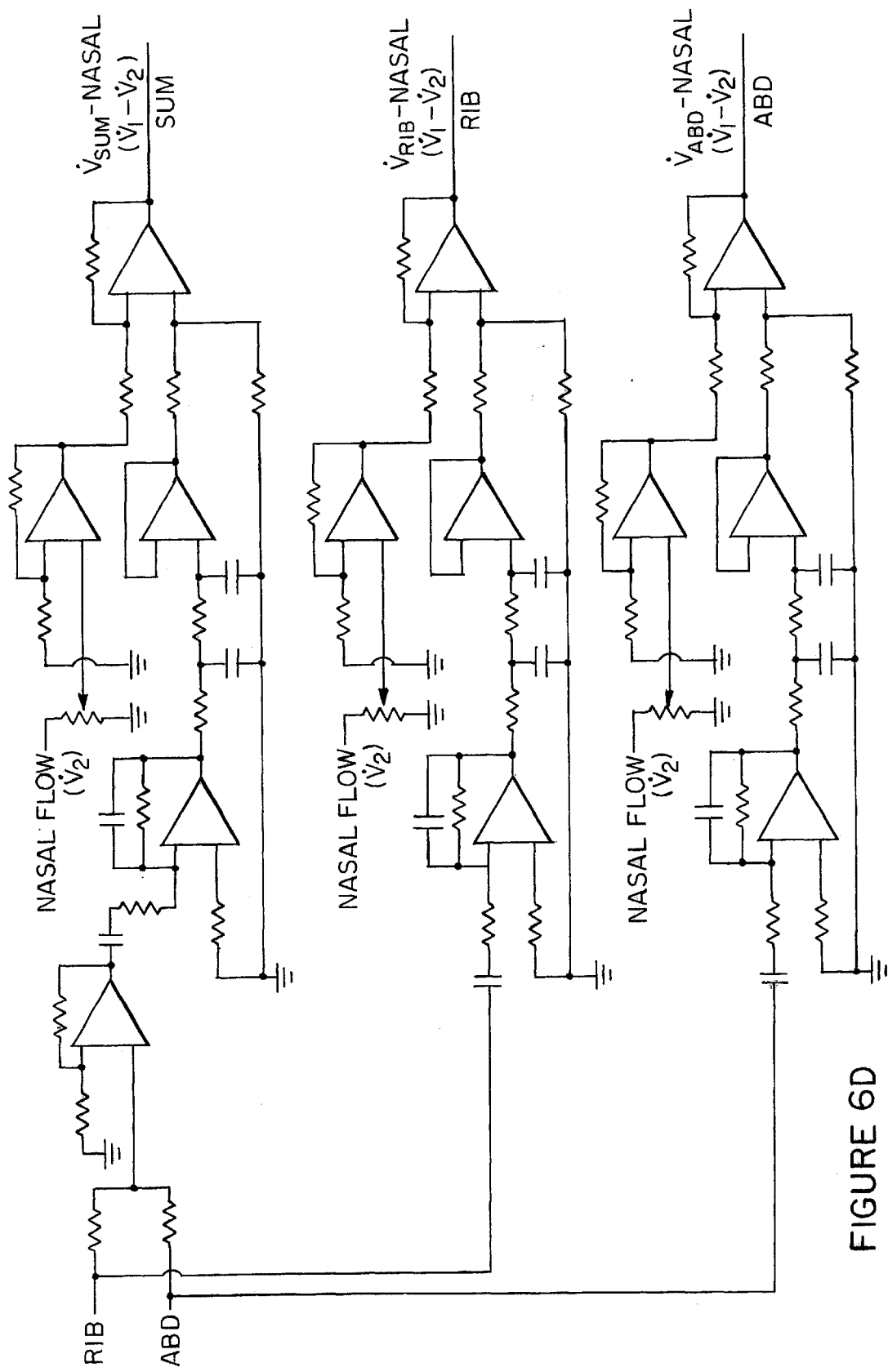
FIG. 6D is a schematic diagram of an exemplary circuit used for analog subtraction as described in FIG. 6C.

Referring to FIG. 6D, an exemplary circuit diagram for the analog subtractor described in FIG. 6C is illustrated. Essentially, the effort signal as measured from the rib cage is summed with the effort signal as measured from the abdominal region to result in a sum signal. The nasal flow signal indicative of the airflow is then subtracted from the sum signal to result in the signal $V_{sum}$-NASAL. In addition, the nasal flow signal is subtracted from the effort signal as measured from the rib cage alone is subtracted from to result in the signal $V_{rib}$-NASAL. Further, the nasal flow signal is subtracted from the effort signal as measured from the abdominal region alone to result in the signal $V_{abd}$-NASAL.

Figure 7:
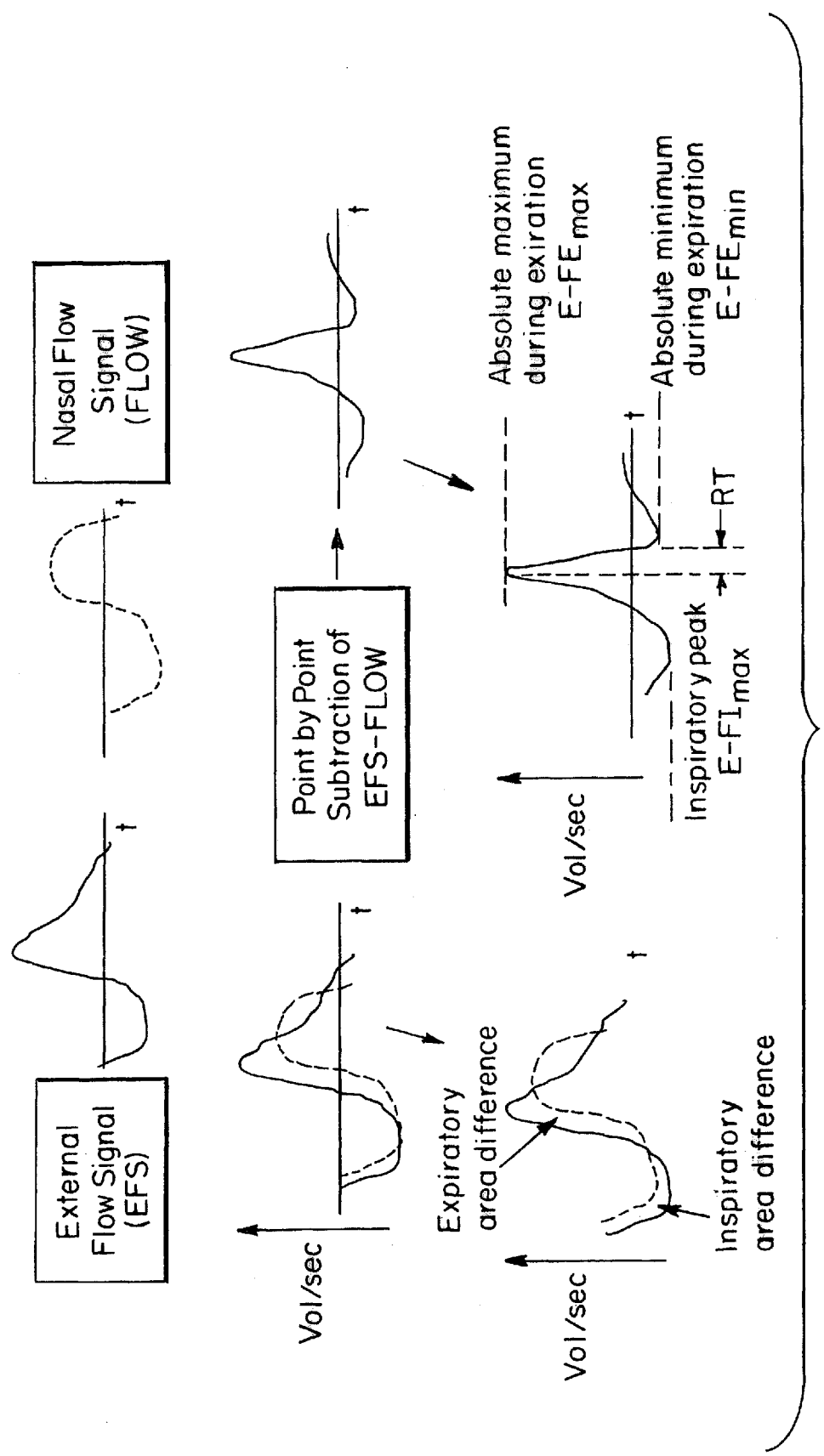
FIG. 7 illustrates graphically the signals that are processed in accordance with the present invention.

Referring to FIG. 7, the signals as measured, both the external flow signal (EFS) which represents the effort signal and the nasal flow signal which represents the true airflow signal, are graphically illustrated. The figure further illustrates the two methods that may be used to compare the differences between the effort and flow signals. A first method includes a point-by-point subtraction in the time domain of either analog or digital signals indicative of external flow and the flow which then results in a signal indicative of a composite waveform, from which the absolute maximum flow during expiration, and absolute minimum flow during expiration can be gauged. In addition, a second method includes the comparison of the waveforms by overlapping waveforms to result in a visual expiratory area difference or an inspiratory area difference.

Figure 8A:
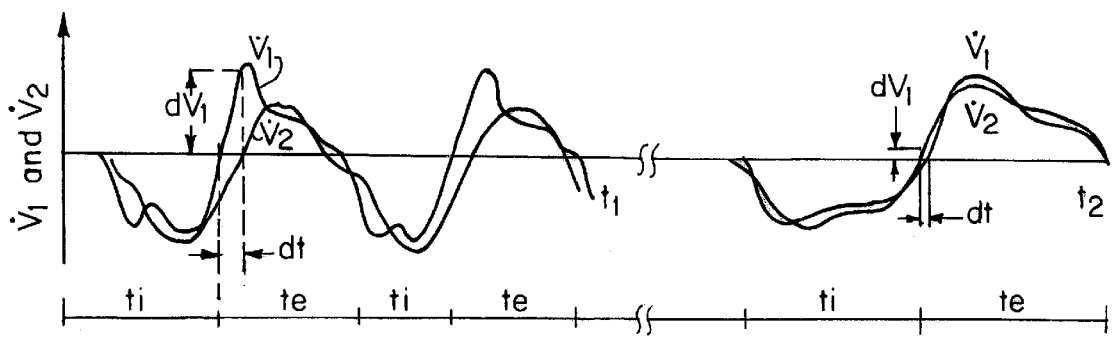
FIGS. 8A–8D graphically illustrate the effort and flow signals measured and processed and their comparison to pleural pressure.
Figure 8B:
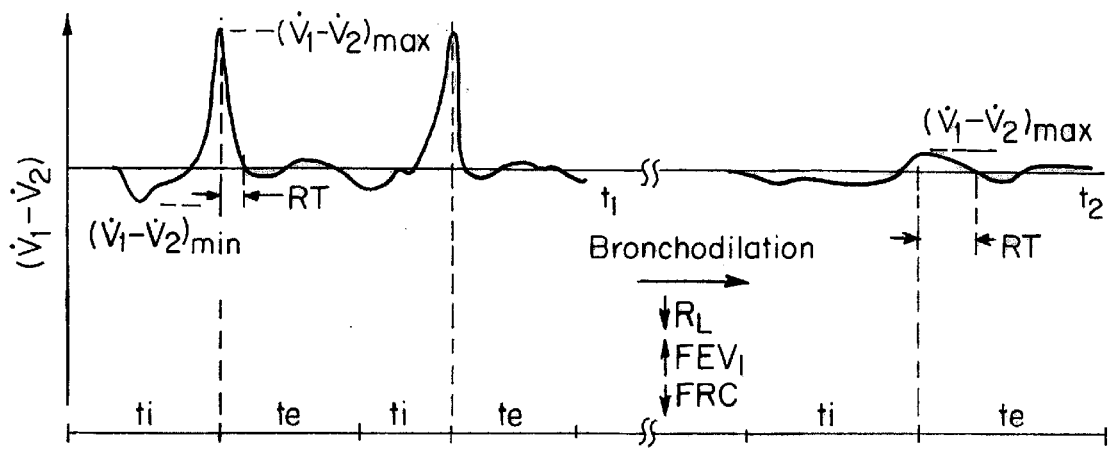
Figure 8C:
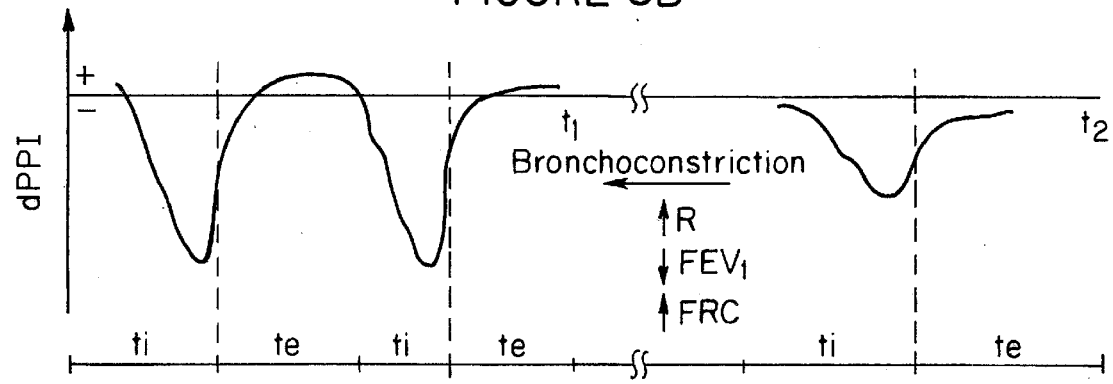
Figure 8D:
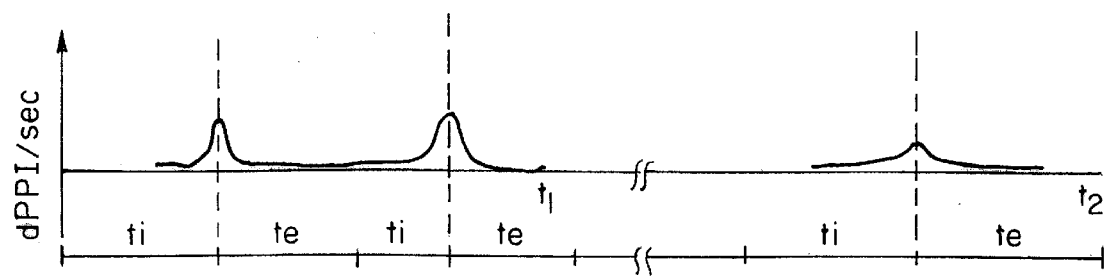

Referring to FIG. 8A, the graphical illustration is a visual comparison of the effort signal $Vdot_1$ and $Vdot_2$ which is the flow signal for a subject having an obstructive pulmonary disease. Upon administration of a bronchodilator the difference both in magnitude and phase between the effort and flow signal are reduced as represented by the later portions of FIGS. 8A and 8B. FIG. 8B graphically represents the composite signal or waveform that results from the point-by-point subtraction of flow from the effort signal achieved in the analog or digital domain. These are then compared to the transpulmonary pressure dPPI signals shown in FIG. 8C and the rate of change of the transpulmonary pressure signal shown in FIG. 8D which is a standard for measuring obstructive pulmonary disease. The peak acceleration of dPPI coincides with peak $Vdot_1$–$Vdot_2$ which shows that the latter is the result of gas compression and airway resistance in the chest. The system of the present invention may be used for monitoring obstructions, or monitoring relief of obstructions during bronchodilation and for monitoring bronchial challenge with a bronchoconstrictor agent as the composite waveform provides a visual indication of obstructions or changes in the physiology of the subject after administering bronchodilators or bronchoconstrictors.

Figure 9A:
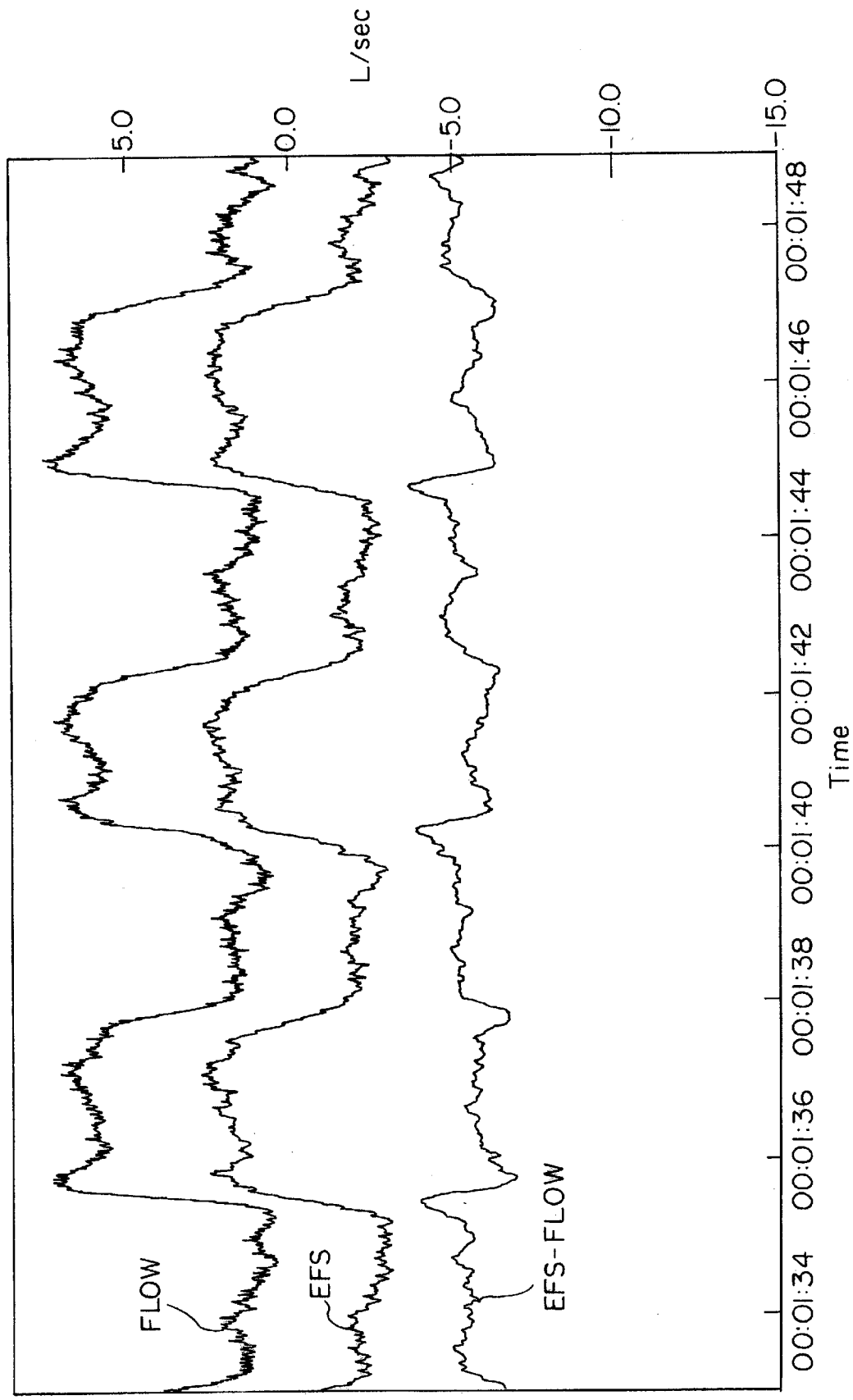
FIGS. 9A–9B graphically illustrate the effort, flow and comparative signals as measured and processed from an equine subject in accordance with the present invention.
Figure 9B:
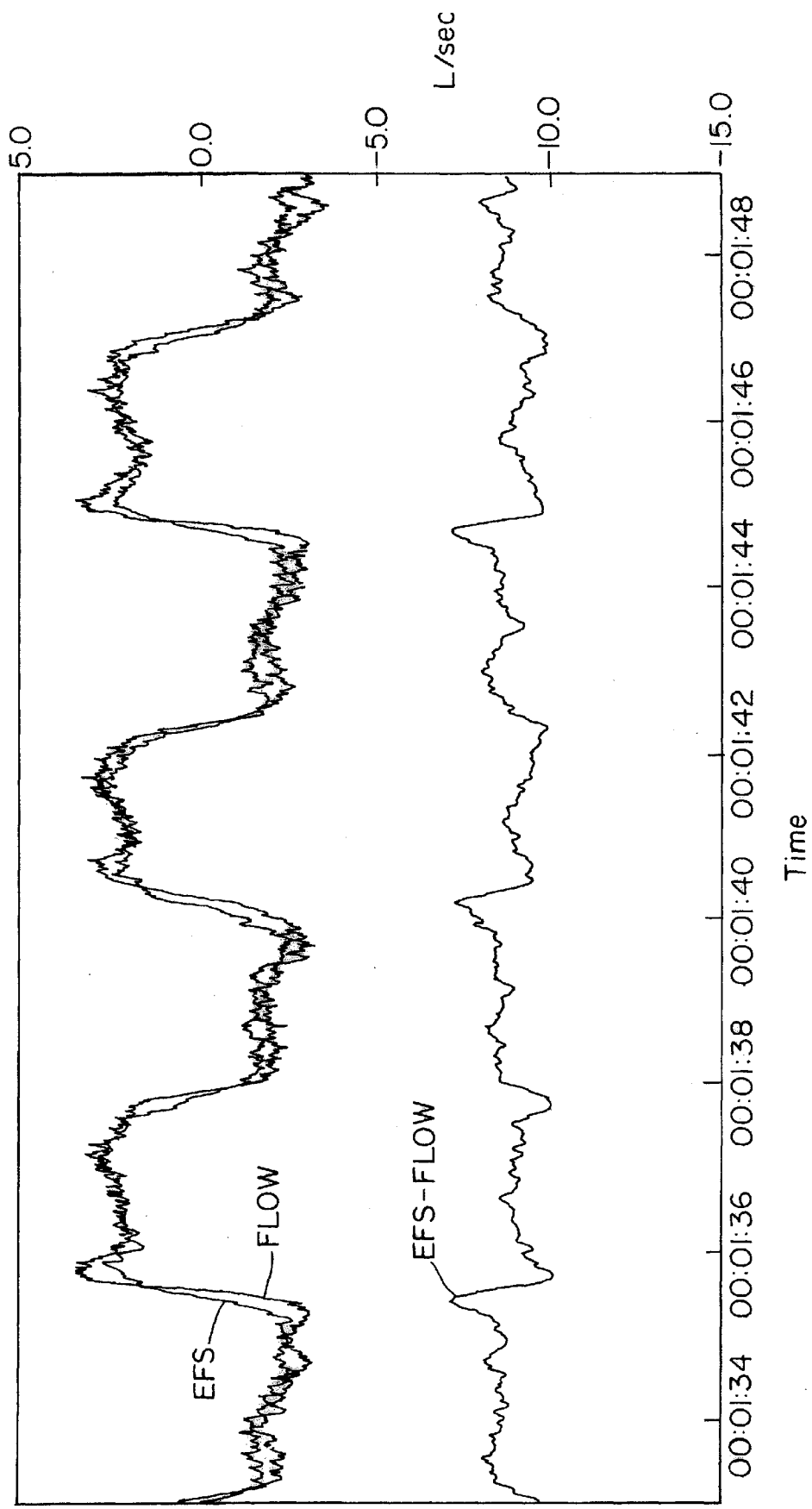
Figure 10A:
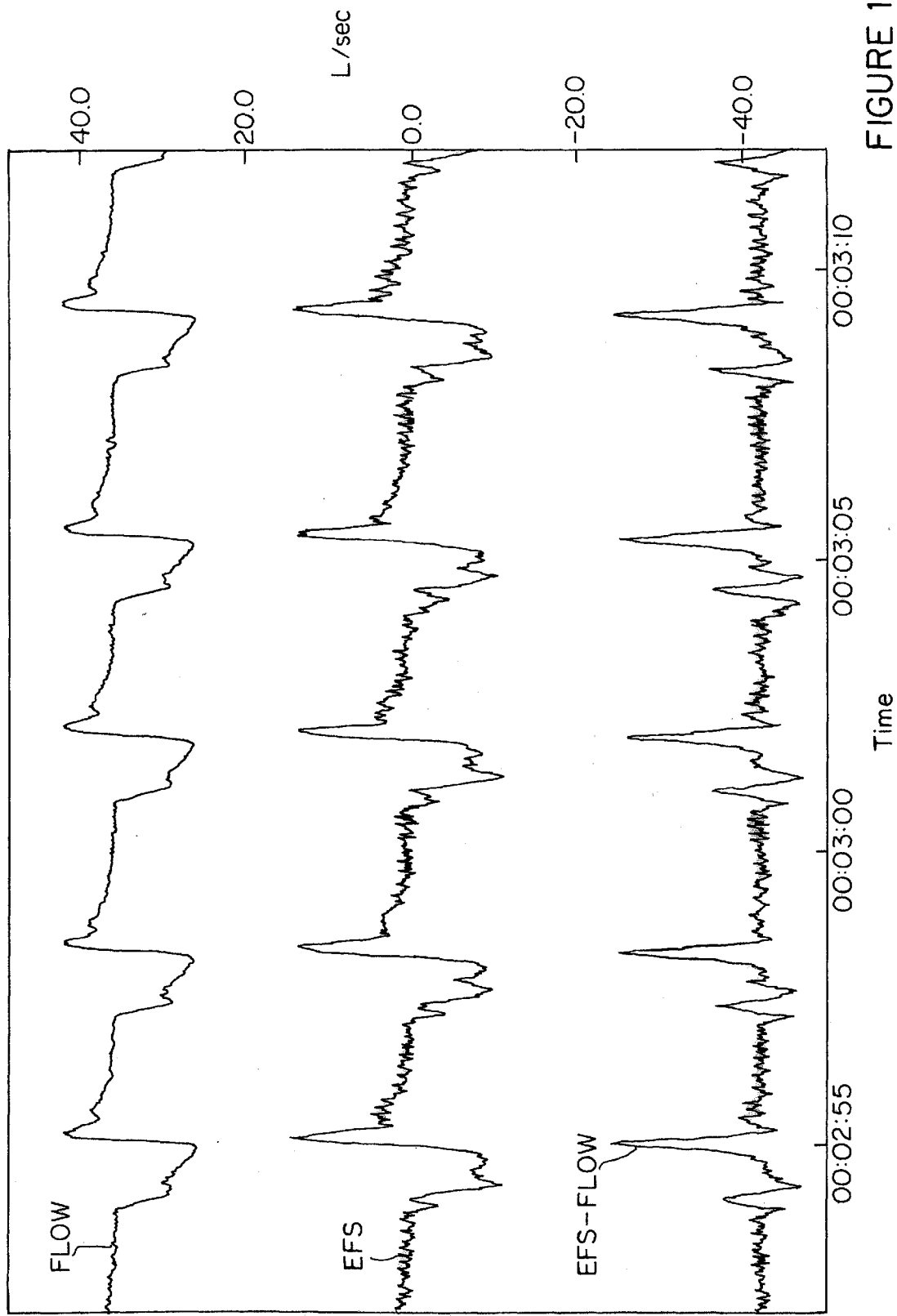
FIGS. 10A–10C graphically illustrate the effort, flow and comparative signals as measured and processed in accordance with the present invention from an equine subject with chronic obstructive pulmonary disease.
Figure 10B:
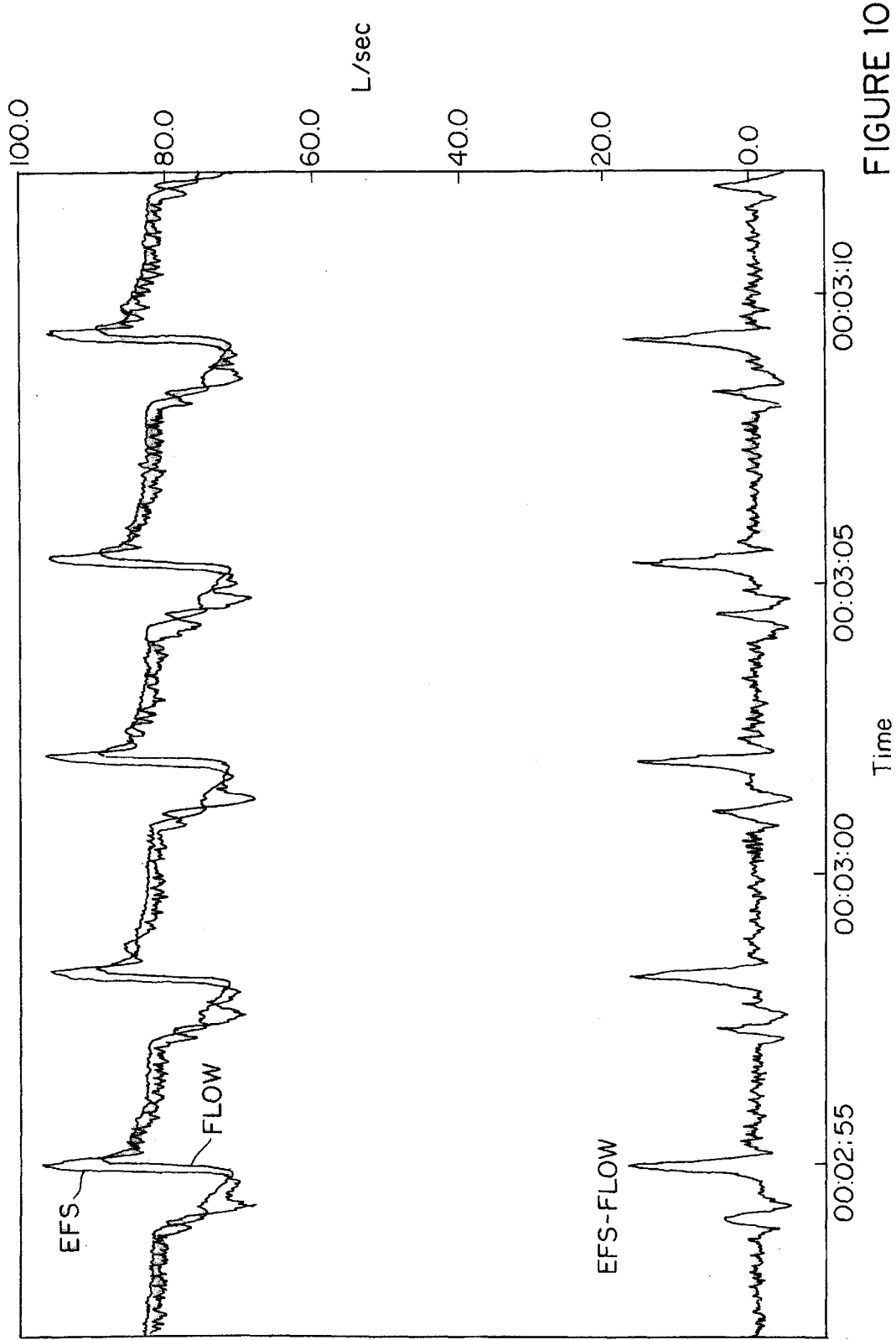

Referring to FIGS. 9A and 9B, lung dysfunction can be measured by comparing an external measurement of flow (EFS) with flow measured at the airway opening in exactly the same time domain. FIGS. 9A and 9B provide an example of the processing of signals in a normal equine subject without an airway obstruction. Flow closely matches the EFS signal in a normal horse in that there is no or minimal phase lag or magnitude difference. FIGS. 10A and 10B provide examples of the effort and flow waveforms of an equine subject with chronic obstructive pulmonary disease. The two component waveforms of effort and flow are compared by overlapping or by actually subtracting point-by-point, true flow from the external flow signal, to obtain a third composite waveform which is depicted in FIG. 10A and 10B as the signal indicative of EFS-flow. The overlapping of waveforms allows quantitative comparisons based on the phase lag and magnitude differences between the signals. Aspects of the composite waveform (external flow signal-flow) can be measured directly using various dimensions and time related data that measure lung dysfunction. The individual component and composite waveforms provide signals for real time visual monitoring. The comparison of the two measures of flow, both external flow and true flow, in the same time domain is an important part of the present invention as both the magnitude and phase relationships are compared.

Figure 10C:
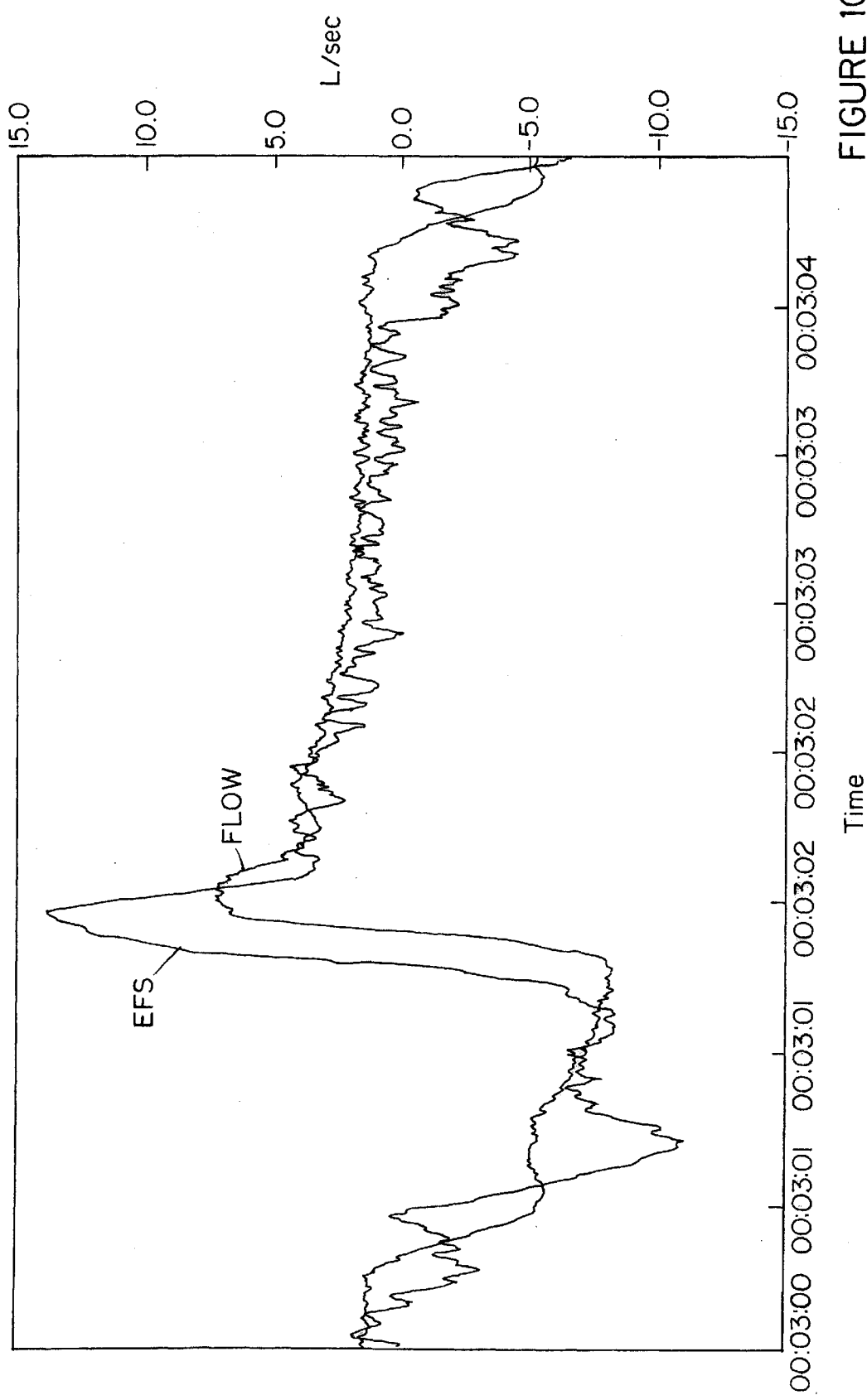

Referring to FIG. 10C, the phase lag between the external and flow signals in the horse with chronic obstructive pulmonary disease, is illustrated. The EFS signal leads the flow signal. An important feature of the methodology of the present invention therefore, is to examine the asynchrony of waveforms. The more asynchronous, i.e., the greater degree of phase lag observed for nasal flow, the greater is the airway obstruction. The difference in magnitude and phase between external and nasal flow correlates well with measures of pulmonary resistance and dynamic compliance. Asynchrony can be transient and instantaneous, but highly significant.

Differences in phase and magnitude between external and nasal flow measurements correlates with classical measurements of impedance. This suggests that the methodology of the present invention measures some combination of resistance, elastance, or inertance and the resultant gas compression in airways and lung tissue. Resistance is a component often used to measure the effects of bronchodilators and bronchoconstrictors. Elastance is a factor that describes the tendency of lung tissue to recoil during inflation. If small airways are obstructed, a smaller portion of the lung gets inflated, thus causing an increase in elastance. Inertance, is the force required to accelerate a column of air within the airways. Applying oscillatory mechanics theory, phase and magnitude differences at slow breathing frequencies are explained by the development of gas compression and resistance in small airways and tissues (i.e., changes in elastance and resistance). At higher breathing frequencies, the methodology of the present invention detects gas compression and resistance in larger airways (i.e., changes in inertance and resistance). As the present invention incorporates an external sensor of flow at the body surface, its output reflects respiratory drive and passive events, such as, lung elastic recoil and chest wall recoil and an effect on any of these components effects the external signal. It is emphasized that in the present invention external flow is compared with true flow. If one compares external flow or acceleration as measures of respiratory drive with ventilation also derived from the external sensor, the gas compressive effects will not be evident and a phase lag will not be measurable. This distinguishes the concepts of prior art which suggest the simultaneous use of external sensors for the measurement of respiratory drive and ventilation.

The methodology of the present invention, provides an indication whether the difference between external and nasal flow is occurring during the expiratory, as shown in FIGS. 10B and 10C, or during the inspiratory portions of the breath. This aids in determining the location of the obstruction. Differences in magnitude and phase of the two component waveforms during inspiration, suggest that a more proximal obstruction exists, and differences observed during expiration suggests a distal airway obstruction. External and nasal flow have to be compared in the same time domain, using both positive and negative scales to examine these phenomena real-time. This simplifies the monitoring of a patient by inspecting a single waveform.

Figure 10D:
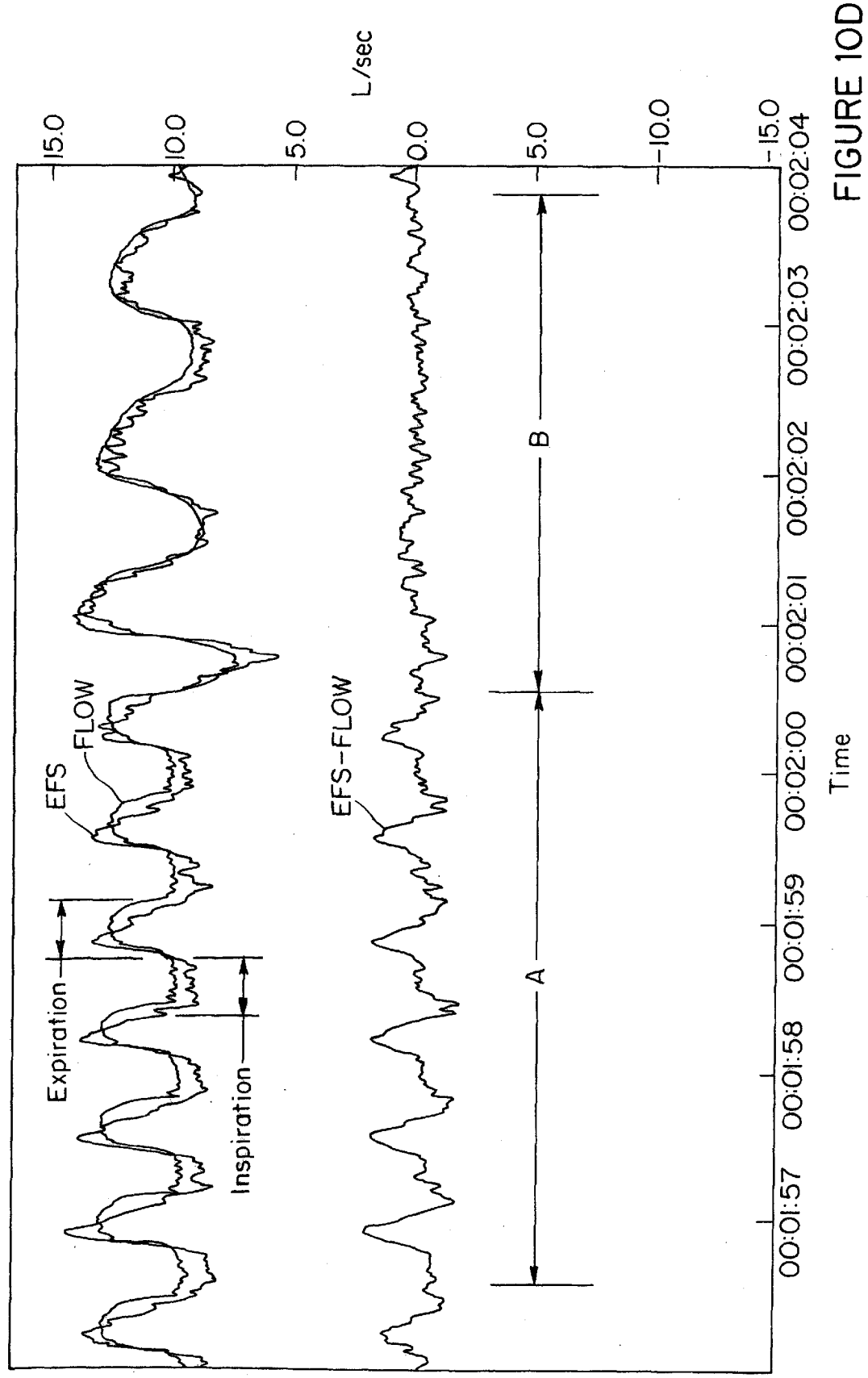
FIG. 10D graphically illustrates the effort, flow and comparative signals as measured and processed from a human subject.
Figure 11D:
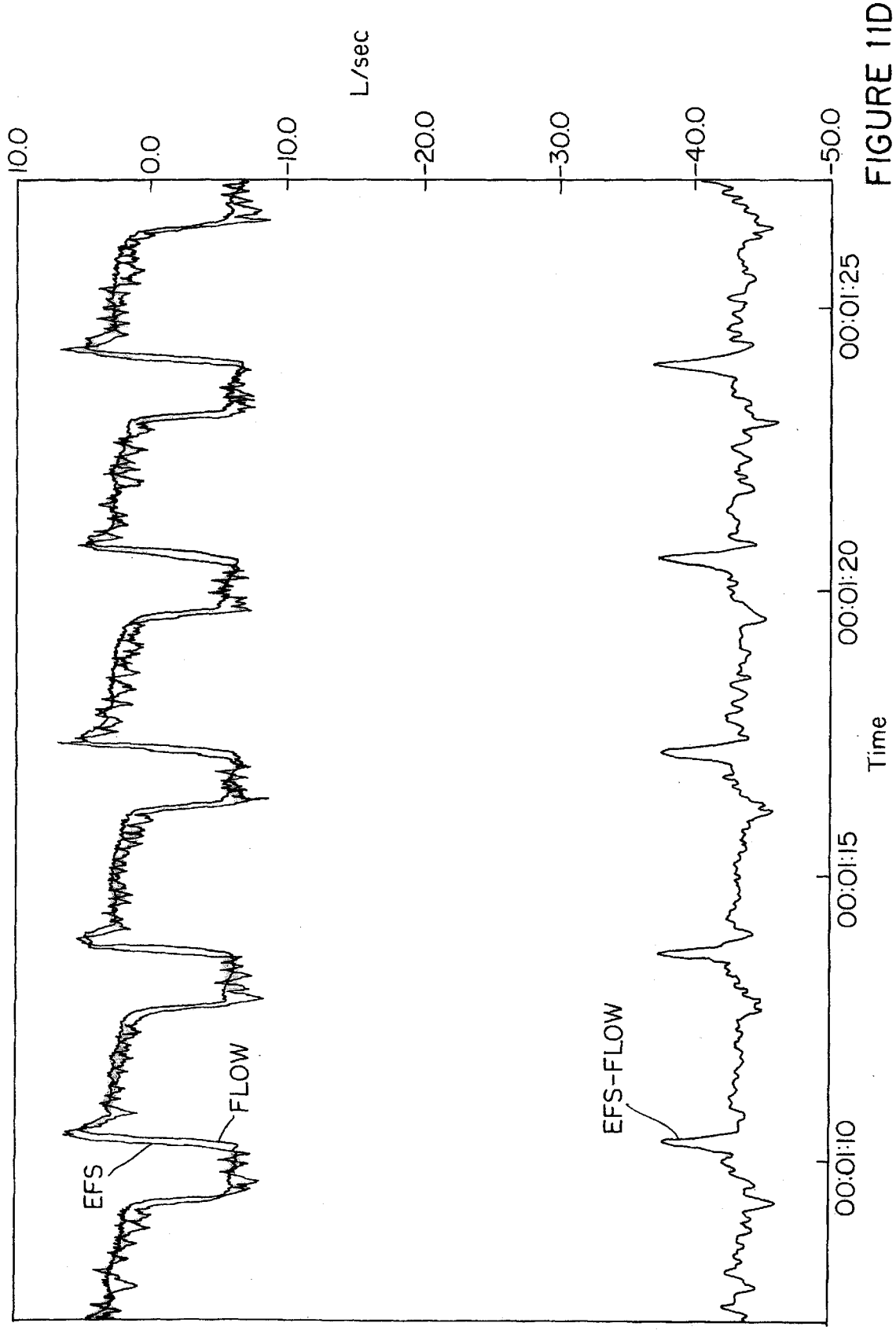
Figure 11E:
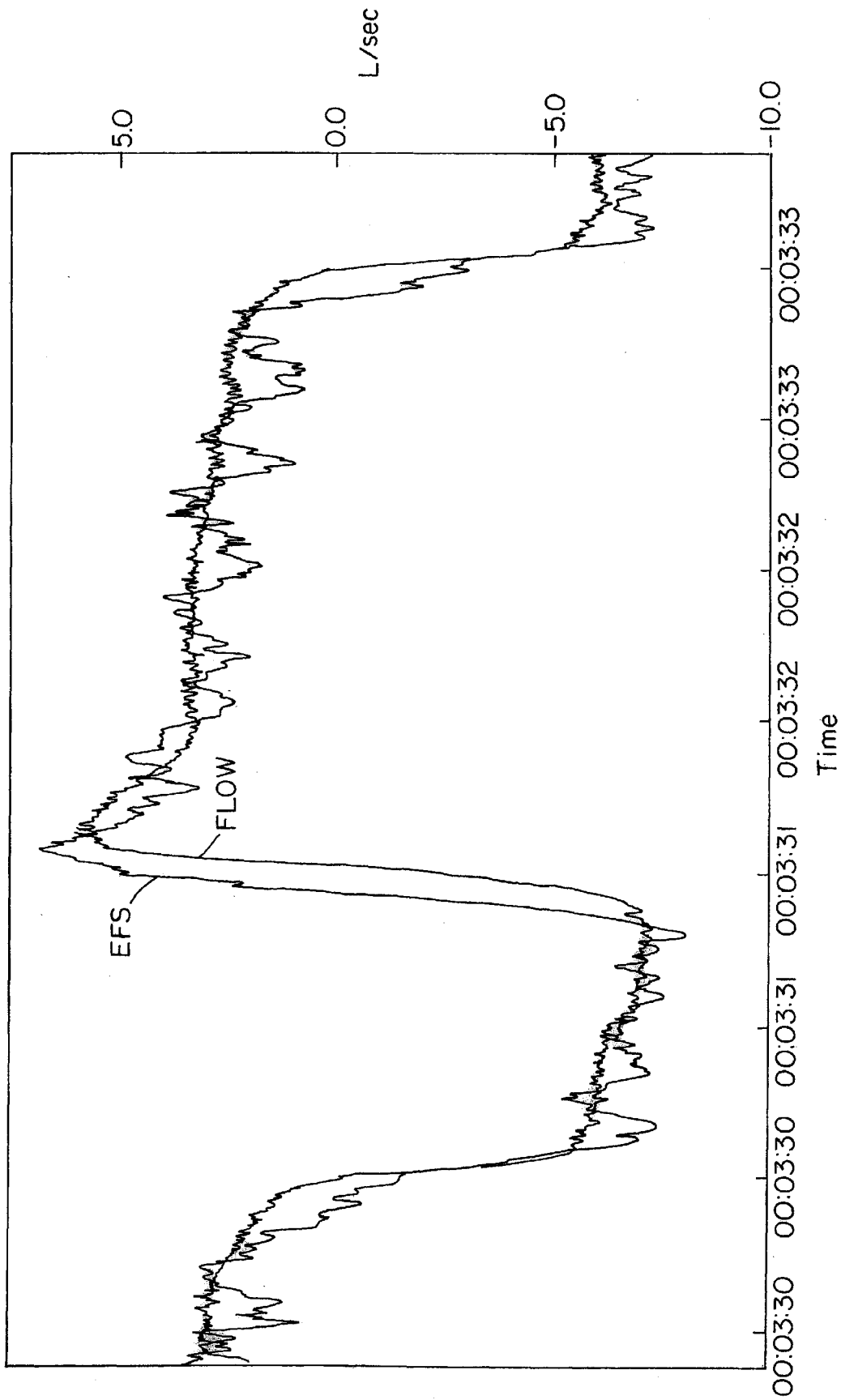

Referring to FIG. 10D, data from a human subject graphically illustrates the effort, flow and comparative waveforms as measured and processed in accordance with the present invention. Segment A is associated with a time period when the human subject had an airway obstruction. Differences in magnitude and phase of the two component waveforms of EFS and flow are relatively more pronounced during the inspiratory phase of the breath (which correlates with the valleys in the waveforms). This suggests that the obstruction is located in the upper airway or a more proximal obstruction exists. If the magnitude and phase differences of the two component waveforms of EFS and flow were relatively more pronounced during the expiratory phase of the breath, then the location of the obstruction would be located in the lungs and thus a distal airway obstruction is suggested. Therefore, the present invention provides an additional benefit of instantaneously providing location information regarding the airway obstruction. Segment B is associated with a time period when the human subject can breathe normally and is not influenced by an airway obstruction. The magnitude and the phase of the component waveforms track each other and there are no pronounced differences. The composite waveform (EFS-Flow) is relatively quiescent compared to the composite waveform segment representative of an airway obstruction.

The following tabulation for human subjects shows the correlation between a conventional measure of upper airway resistance to the composite waveform (EFS-Flow) peak amplitude as measured and processed in accordance with the present invention. The resistance of 1 $cmH_2O$/Liter/second corresponds to normal breathing without an airway obstruction. The peak amplitude of the composite waveform of 0.5–0.75 corresponds to a state of normal breathing without an airway obstruction in accordance with the present invention. As the resistance increases with increase in an obstruction of the upper airway, from 5 to 10 $cmH_2O$/Liter/second which relates to a moderate to severe obstruction, the peak amplitude of the composite waveform also increase from 3–4 to 5–7 Liters/second.

Variable
   Resistance ($cmH_2O$/L/second) 1 5 10
   EFS-Flow (peak amplitude) 0.5 3–4 5–7
     (Liters/second)

The present invention can be used for monitoring the effects of various medications. As such, the respiration function signal provided after the processing of the input signals is measured before and after various challenges, or treatments are administered, such as, bronchodilators or bronchoconstrictors. The present invention uses bronchodilation response testing to evaluate the level of response of a horse with COPD as an indication for the initiation or continuation of therapy. It should be noted that airflow rates vary according to factors such as species, degree of illness, and body weight. Typically, a bronchodilator, such as albuterol, is administered by metered dose inhalers. In humans, the range of dose is 50 to 100 micrograms, in horses 450–900 micrograms. Bronchodilator treatments result in complete cessation of signs or partial cessation of signs of airway obstruction. In horses, there is typically a reduction in airway obstruction, measured in the form of lung resistance, of about 40 to 60% of a baseline. The composite waveform (EFS-Flow) peak amplitude, upon administering a bronchodilator to a horse, changes from 12.3 to 5.4 liters per second thus indicating a partial cessation of signs of airway obstruction.

Referring to FIGS. 11A–11E, following the administration of a bronchodilator, the patient with lower airway obstruction shows less magnitude and phase differences between external and nasal flow. The change in the waveform is visually obvious, and lends itself to a continuous visual monitoring of a display, similar to monitoring blood pressure or ECG. Following the administration of a bronchodilator to the patient with COPD (shown in FIGS. 10A, 10B and 10C), there is a greater overlap of external and nasal flow waveforms, and the resultant composite waveform synthesized by subtracting the nasal flow from the external flow signals has a smaller amplitude, especially during the expiratory portion of the breath. This indicates resolution of a lower airway obstruction and decreased amount of gas compression in the airways and lung tissue.

Figure 12A:
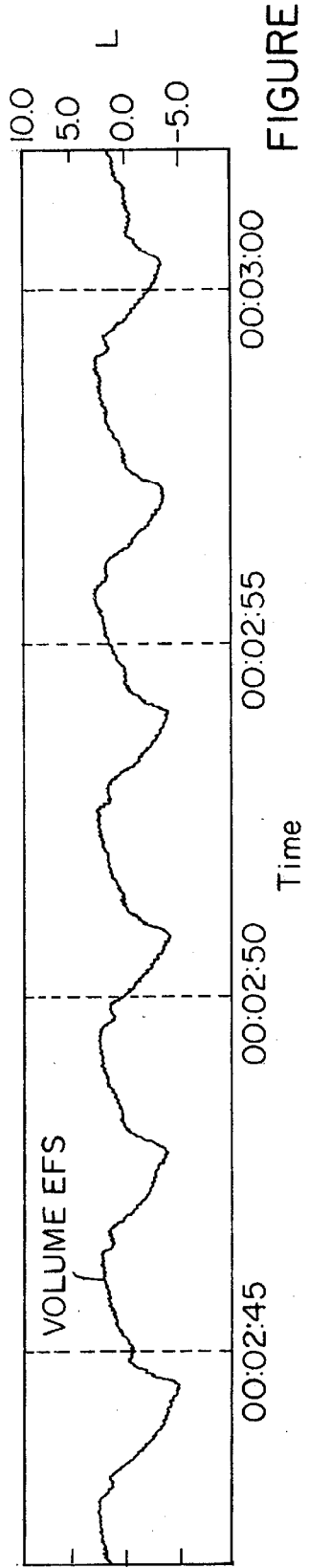
FIGS. 12A–12E graphically illustrate the effort, flow and comparative signals measured and processed from another equine subject having chronic obstructive pulmonary disease.
Figure 12B:
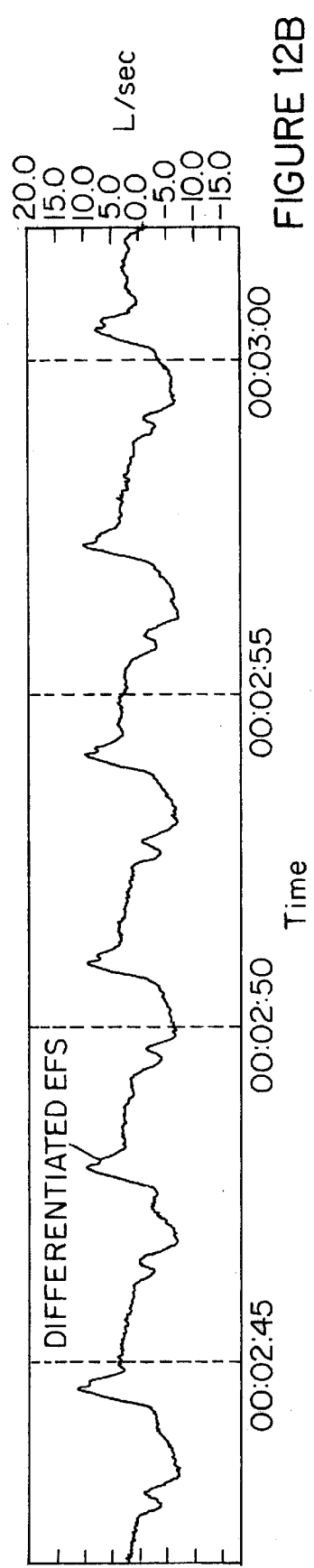
Figure 12C:
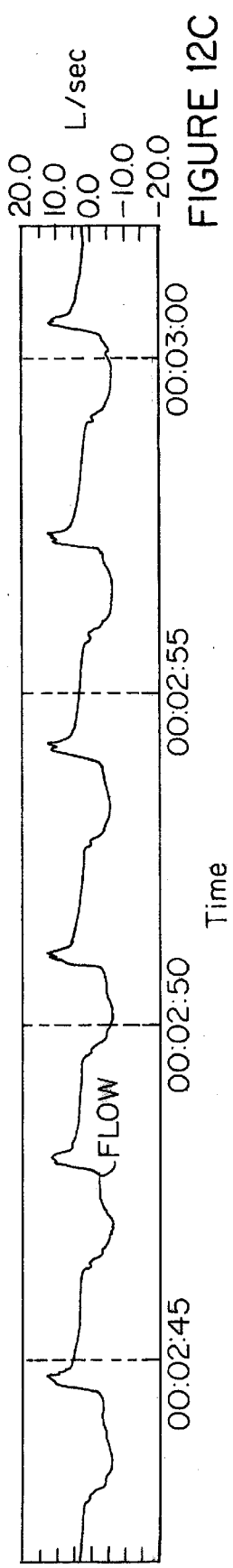
Figure 12D:
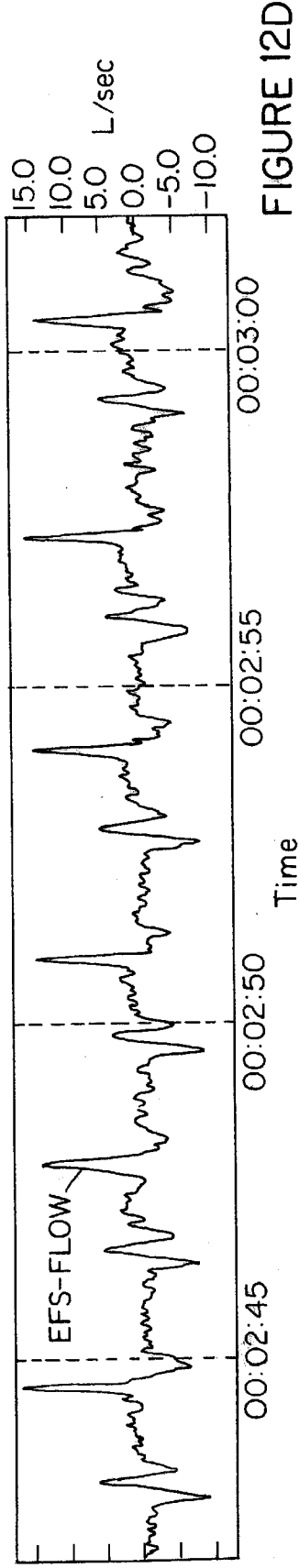
Figure 12E:
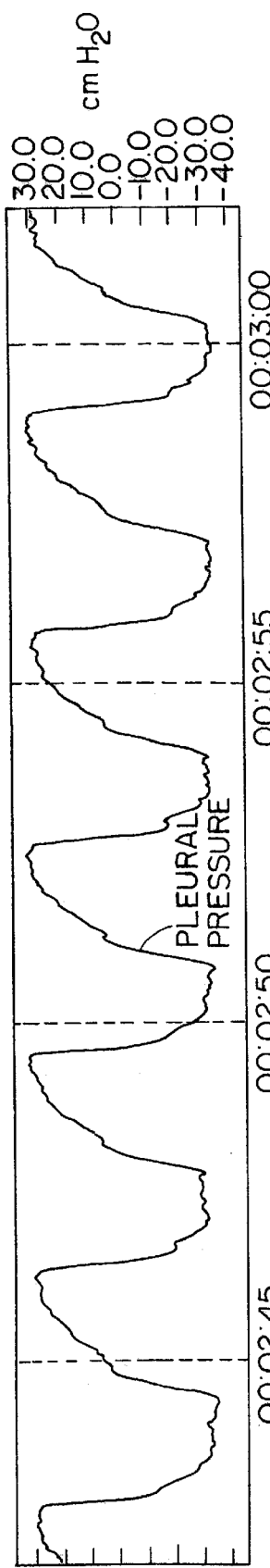
Figure 12F:
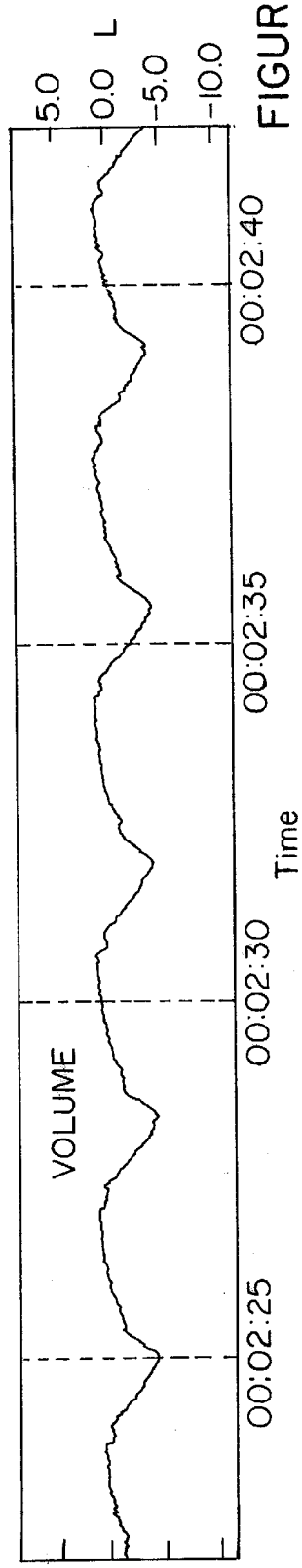
Figure 12J:
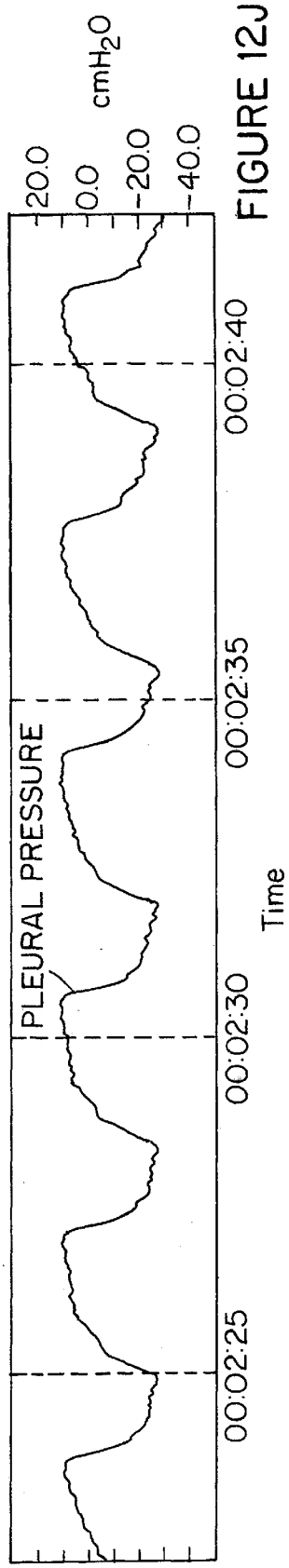
Figure 12K:
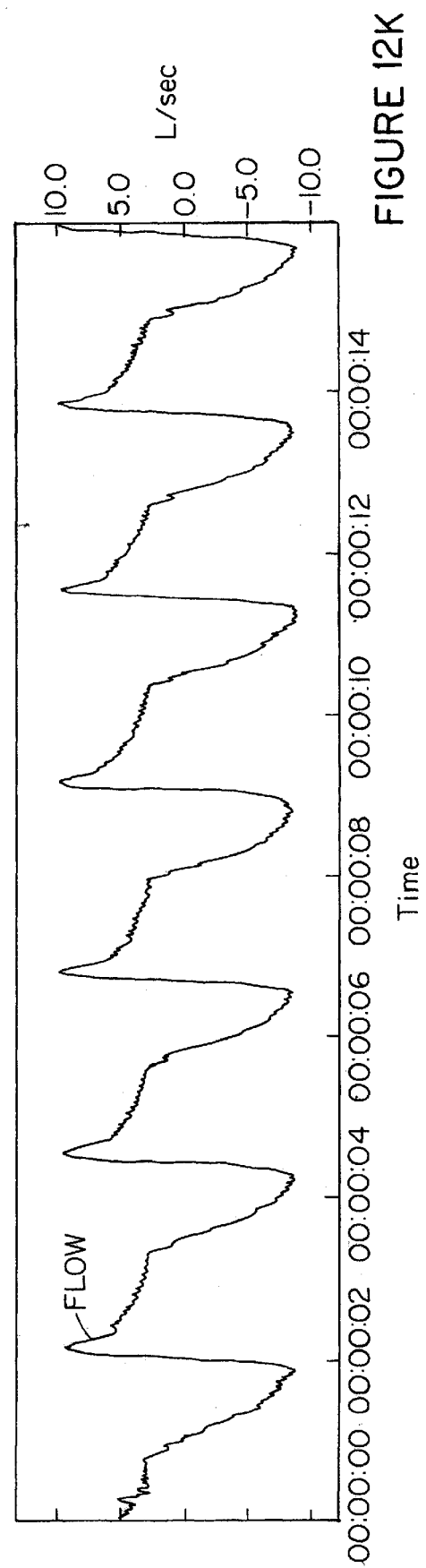
FIGS. 12K–12M graphically illustrate calibrated and normalized flow, effort and comparative signals measured and processed from an equine subject having chronic obstructive pulmonary disease.
Figure 12L:
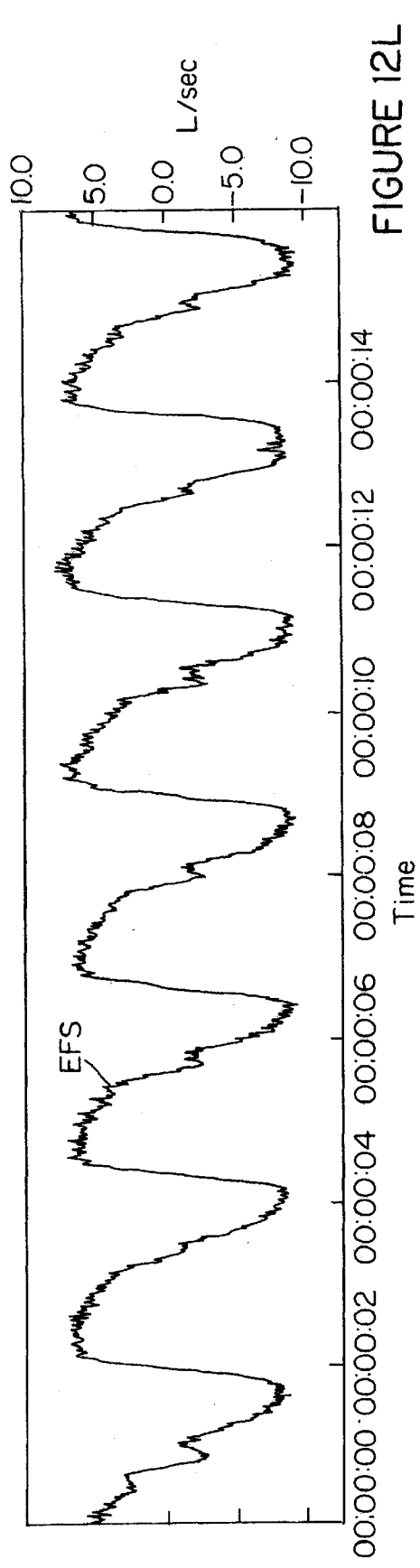
Figure 12M:
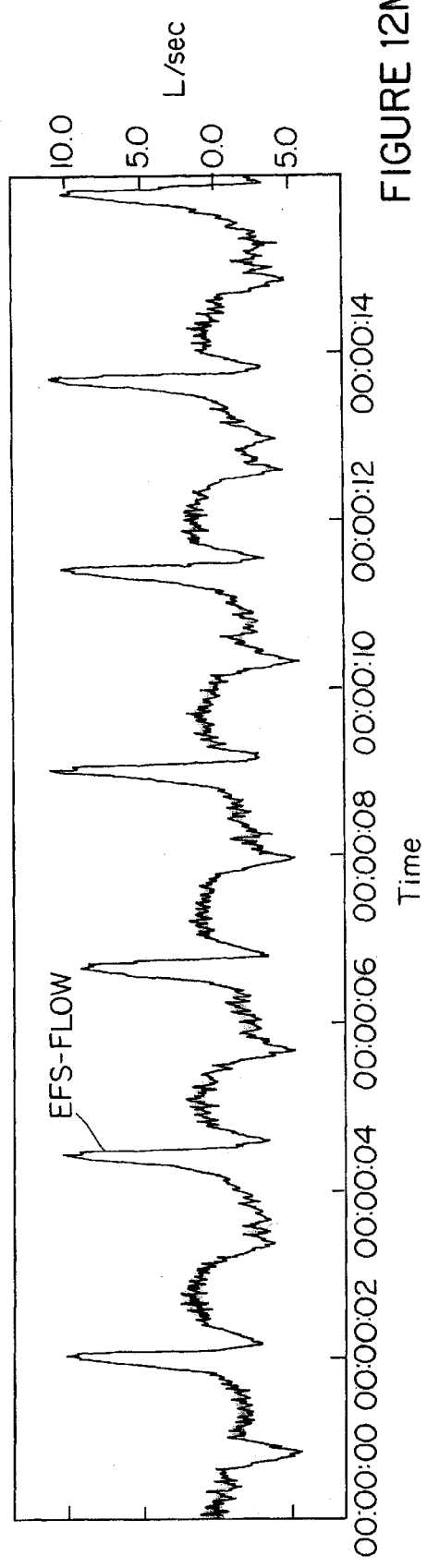

The methodology of the present invention to discern the phase difference between external and nasal flow is important. In some obstructed patients the external measurement of respiratory drive or respiratory drive versus ventilation as an indication of obstruction does not reflect phase difference. For example, there is a marked improvement in the relationship between external and nasal flow, i.e., decreased magnitude and phase differences in equine subjects with COPD after bronchodilation treatment, but only modest changes in the respiratory drive which is the peak of external flow. This is illustrated in FIGS. 12A–12J. There is a change in the appearance of the waveform after bronchodilation as seen in FIG. 12I, which is useful for a monitoring system. There is a characteristic large amplitude spike followed by a rapid descent to below baseline. This rapid descent reflects both an instantaneous phase and magnitude difference, and is used to measure obstruction. The improvements in the difference of the external and nasal flow correlate well (r=0.92) with improvements in transpulmonary pressure, pulmonary resistance and dynamic compliance studied in a group of horses (n=7) with COPD. Thus, the phase differences characterize a fundamental mechanical disturbance in the respiratory function of a patient.

Figure 13A:
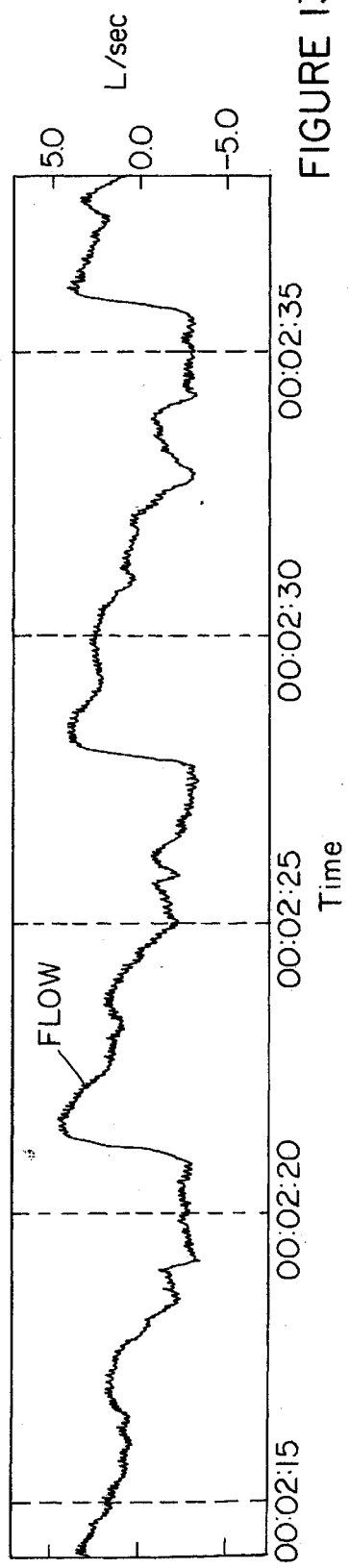
FIGS. 13A–13C graphically illustrates the effort signal measured only from the abdominal region of an equine subject without any airway obstructions, the flow signal and comparative signal determine after processing.
Figure 13B:
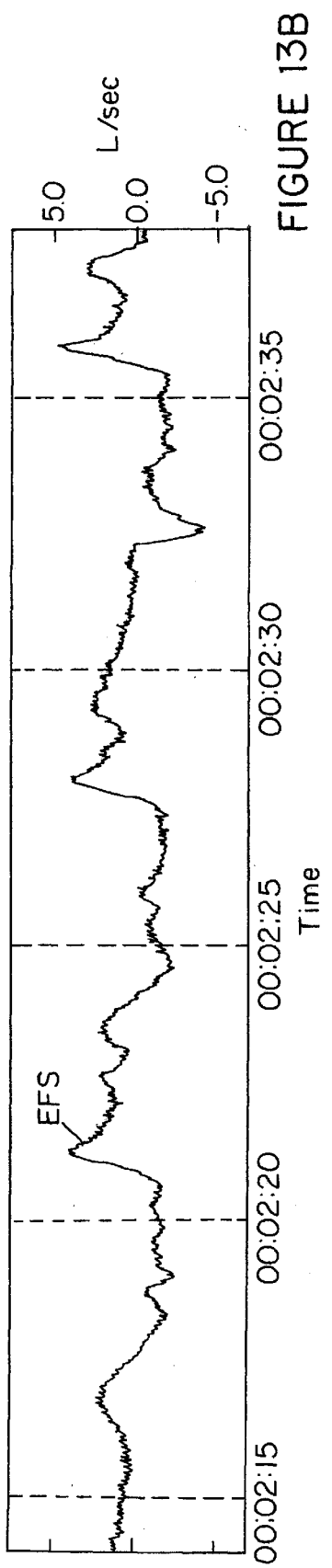
Figure 13C:
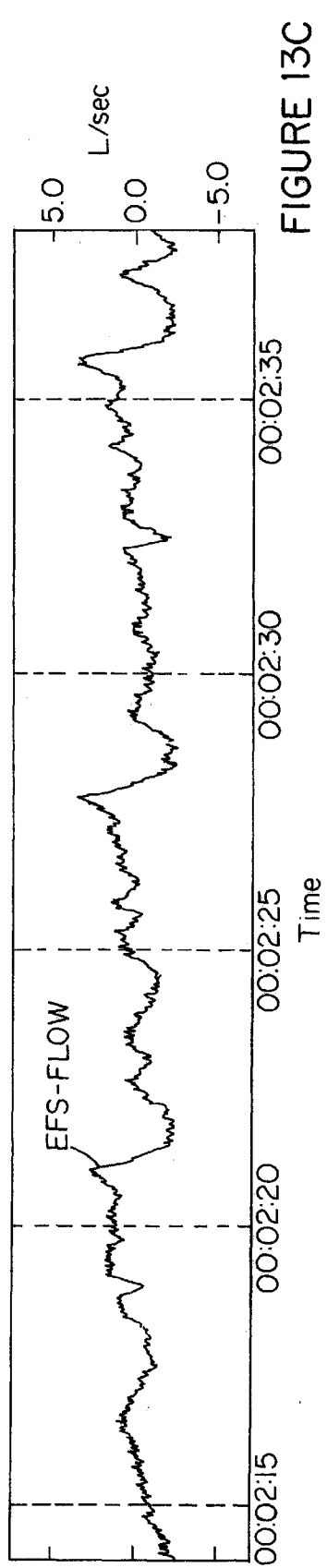
Figure 13D:
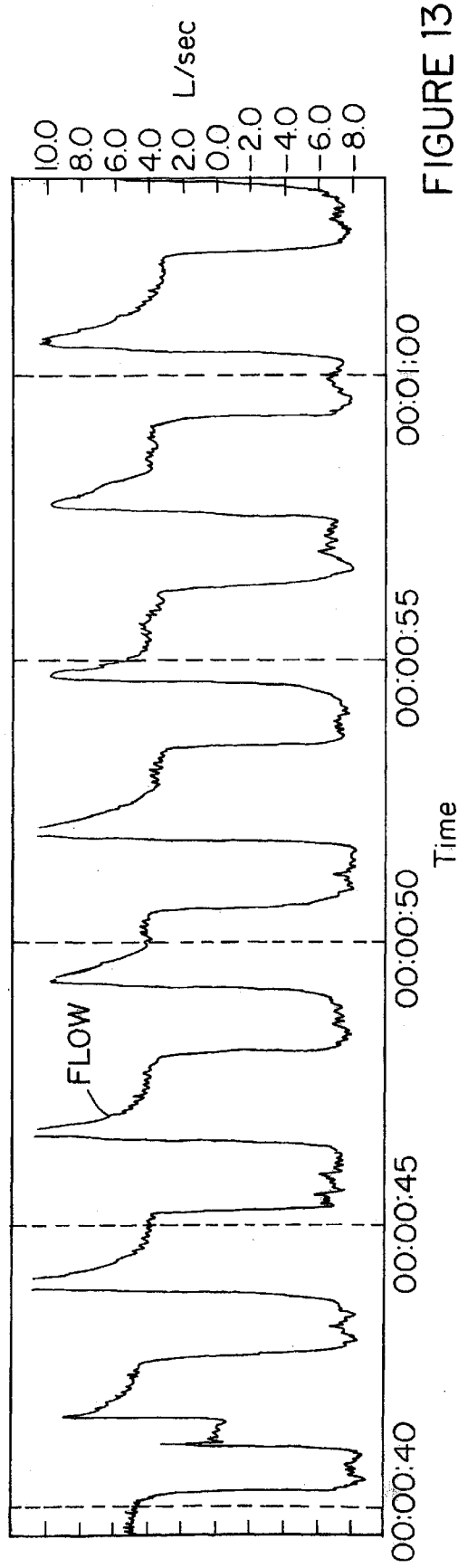
FIGS. 13D–13F graphically illustrate the effects on the effort signal as measured only from the abdomen of the equine subject used in FIGS. 13A–13C, the flow signal and comparative signal after the administration of a bronchoconstrictor.
Figure 13E:
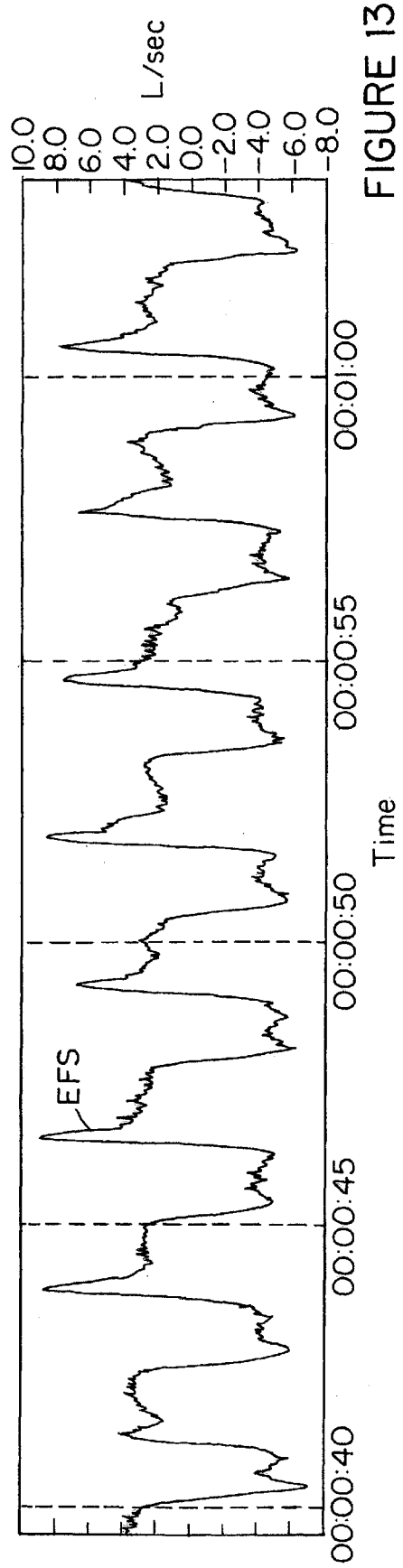
Figure 13F:
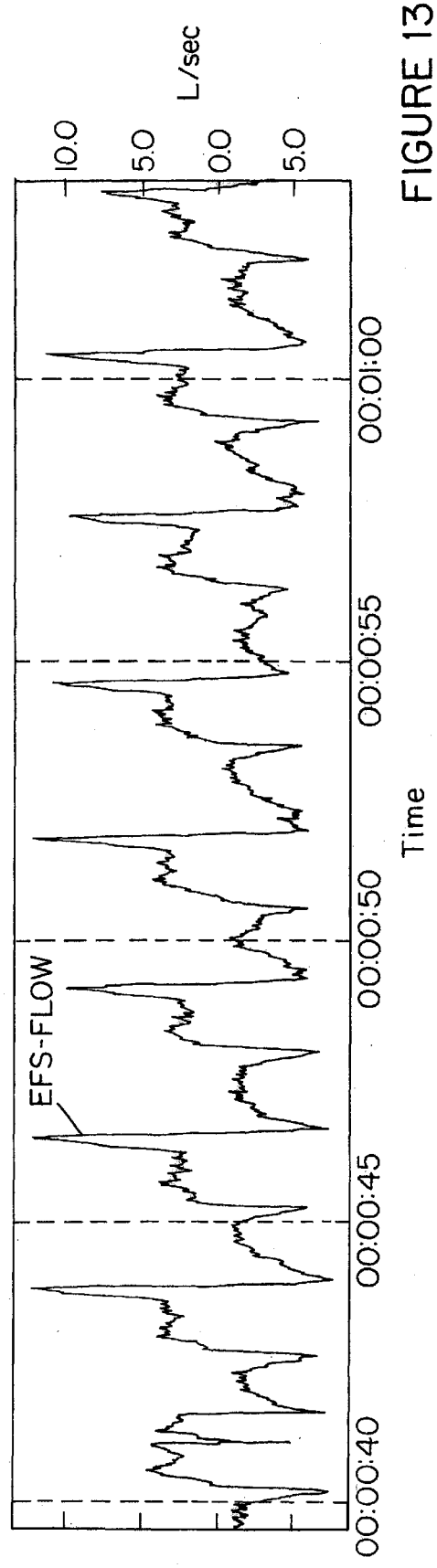

Referring to FIGS. 13A–13F, the administration of histamine to cause bronchoconstriction, on the other hand, results in increased differences in phase and magnitude for external and nasal flow measurements. This results in an increase in the composite waveform magnitude as shown in FIG. 13F. The waveforms from a normal horse before and after administration of histamine aerosol to the lung, as shown in FIGS. 13D–13F, shows an increase in the external minus nasal flow composite waveform (FIG. 13F) during expiration greater than during inspiration, illustrating the expected predominant effect of histamine on lower airways. These graphical illustrations also demonstrate that a single external sensor, placed around the abdomen, for example, could be used to measure bronchoconstriction. Alternatively, the combination of external sensors placed over the rib cage and abdomen can provide signals which can be electronically combined into a sum signal for comparison with flow, and the same results are obtained in the setting of a histamine challenge to the airways.

Referring to FIG. 13G, a tabulation of a classical measure of airway reactivity LogPC65Cdyn, which is the provocative concentration of histamine that decreases dynamic compliance to 65% of a baseline, as compared with a measure of airway reactivity LogPC135SFEmax, which is the concentration of histamine that increases SFEmax to 135% of the baseline, as calculated by the method for measuring respiratory function in accordance with the present invention is provided. For subclinical lower airway obstruction, a test of airway reactivity includes bronchoprovocation of the subject using a histamine (or other chemicals) to evoke bronchospasm as illustrated in FIGS. 13A–13F. A dose response curve is typically generated using a dose range from 1 mg/ml upto 32 mg/ml. The tabulation in FIG. 13G corresponds to data generated from the study of seven horses. A thirty five percentage (35%) increase in EFS-flow peak values (referred to as SFE max) correlated with a thirty five percentage (35%) drop in dynamic compliance, which is a classical measure of obstruction which decreases with airway obstruction. The correlations were greater than 0.9 (p<0.05) for Spearrmans rank correlation coefficient. This data illustrates that a simple point-by-point subtraction of the airflow signal from the effort signalsprovides evidence of transient gas compression and airway resistance during histamine challenge, and the methodology of the present invention can be employed effectively to measure airway reactivity.

Figure 14A:
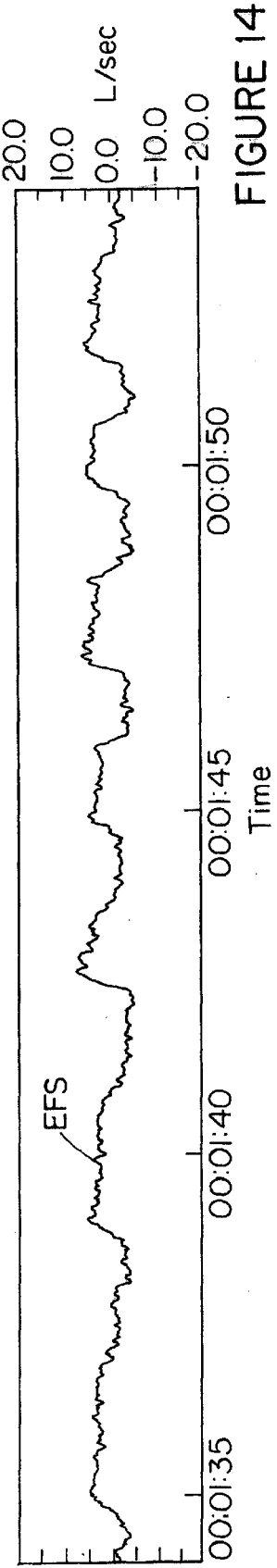
Figure 14B:
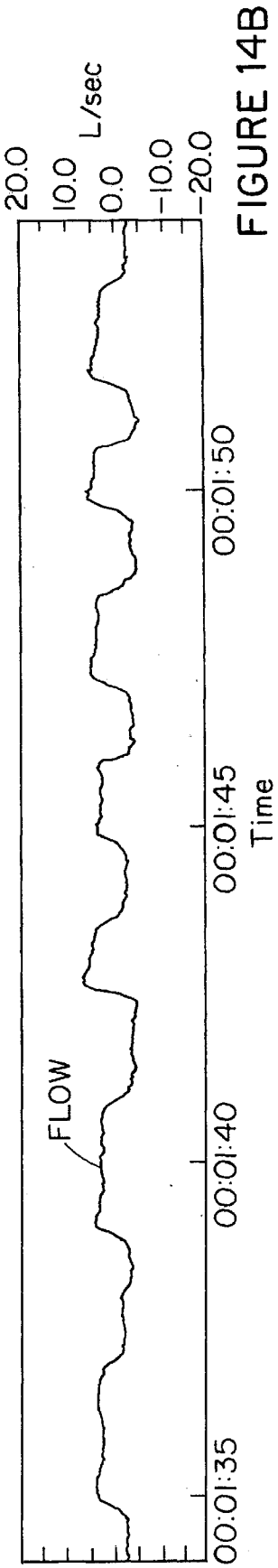
Figure 14C:
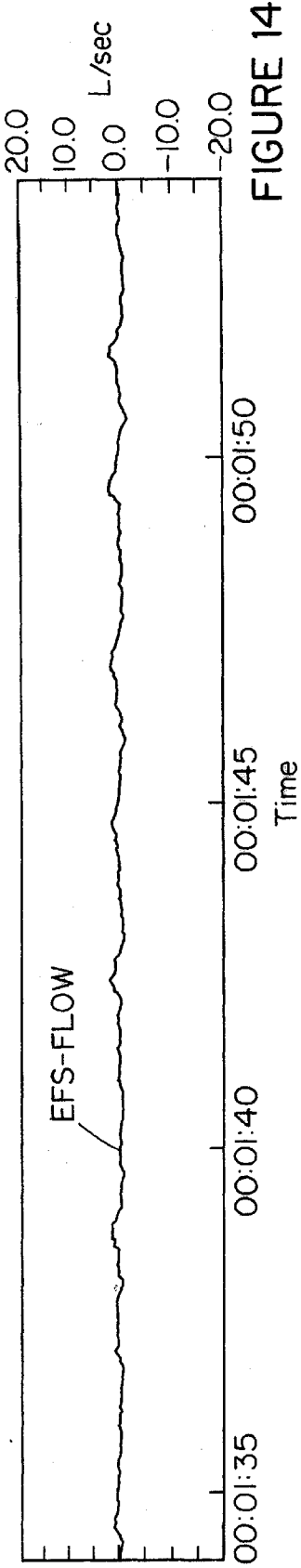
Figure 14I:
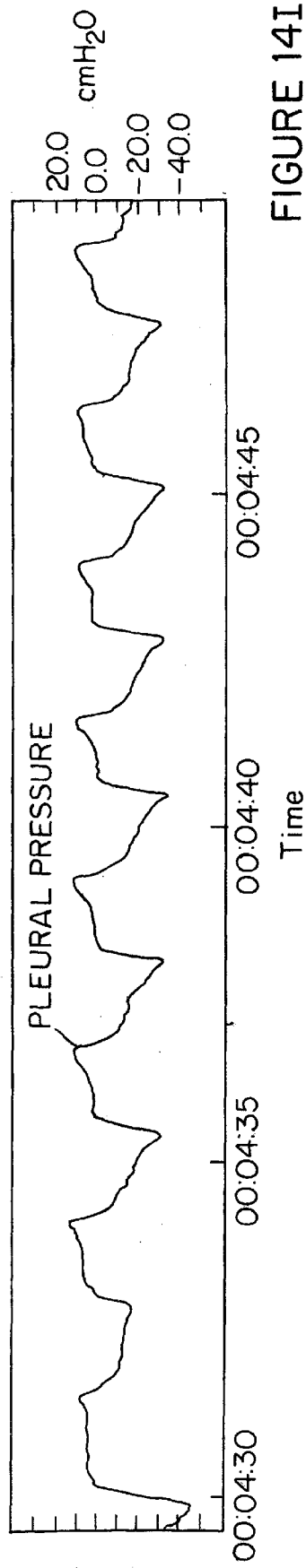
Figure 14J:
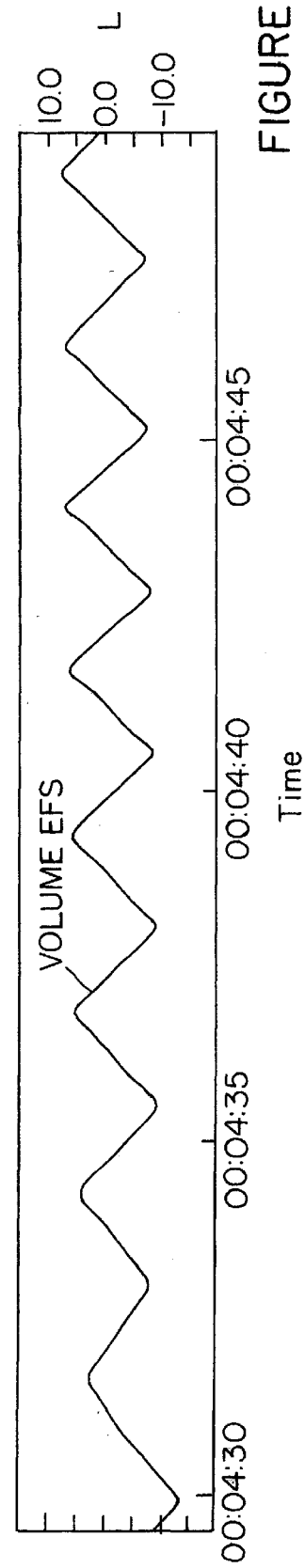
Figure 15A:
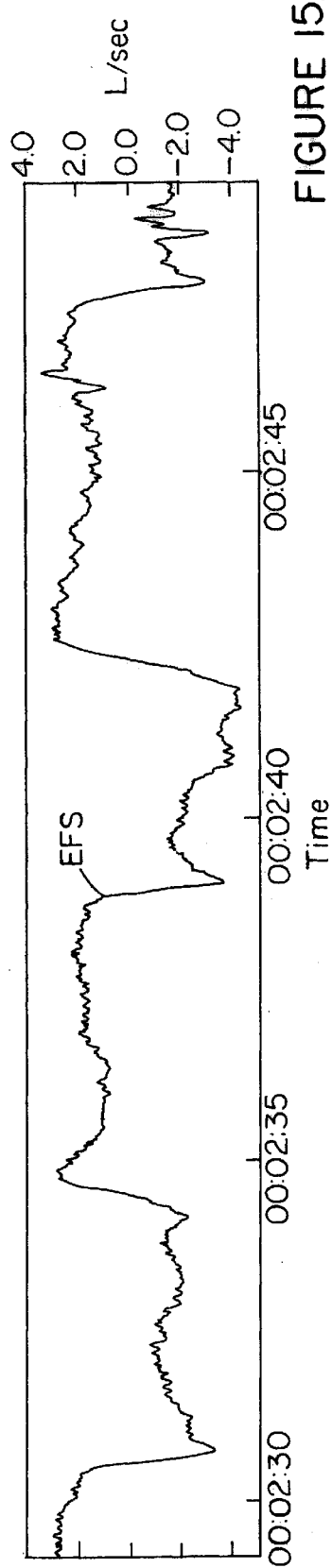
Figure 15B:
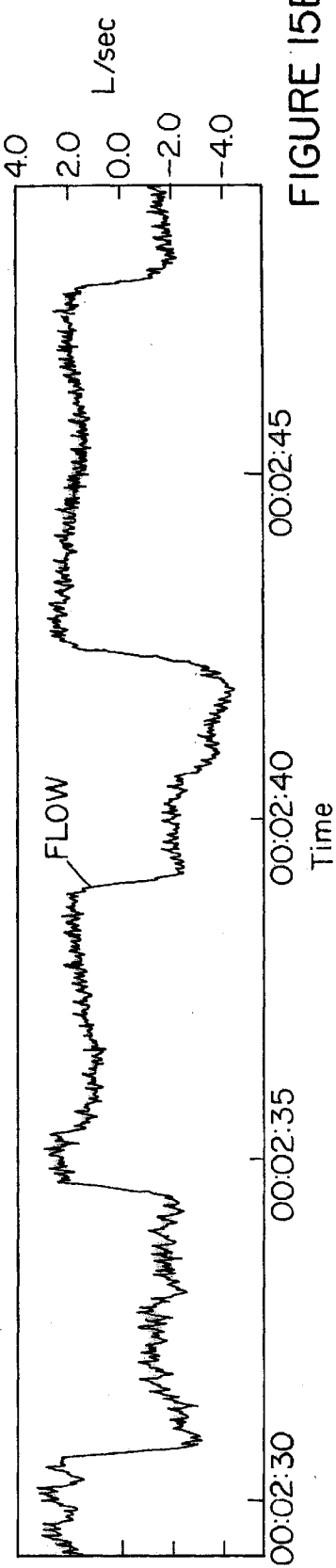
Figure 15C:
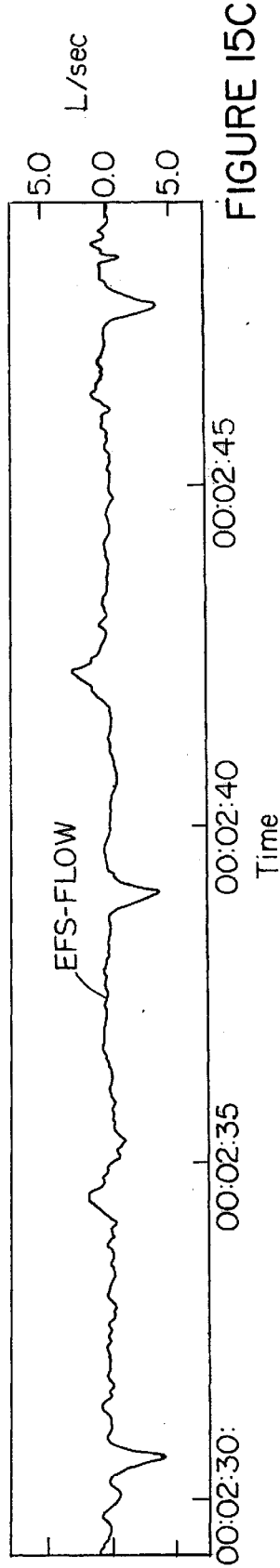
Figure 15G:
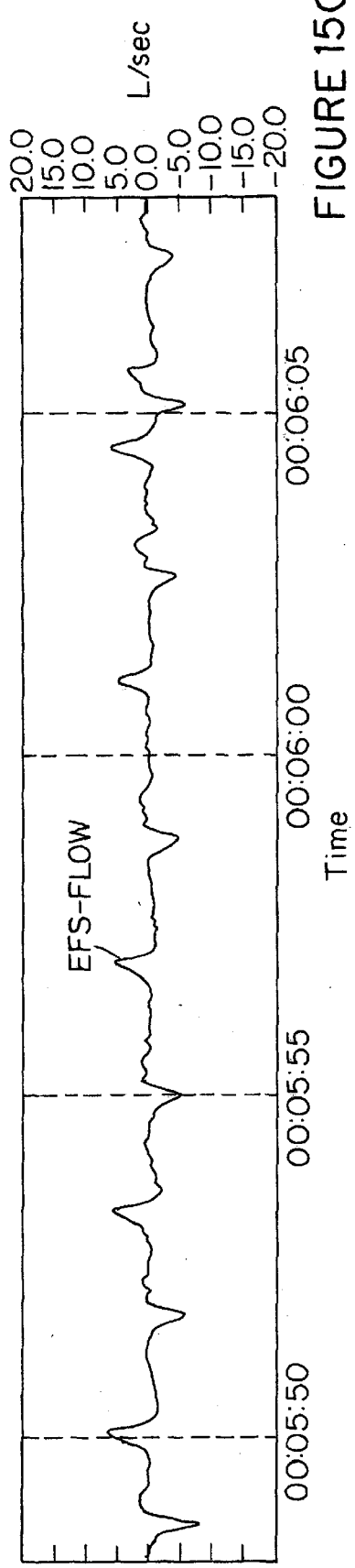
Figure 15H:
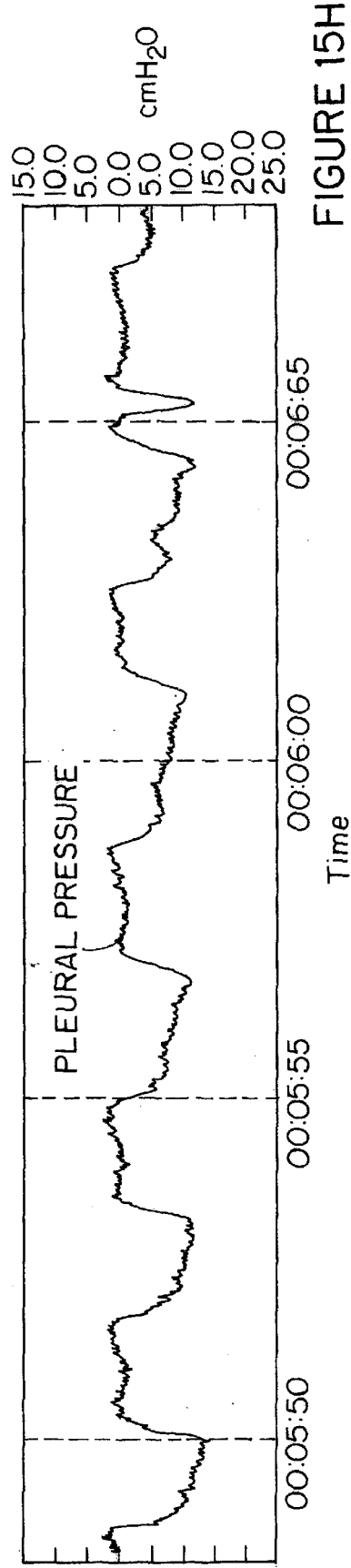

Referring to FIGS. 14A–14J and 15A–15H, examples of changes to the respiratory function during hyperventilation are illustrated. Hyperventilation is an increase in the rate of moving volume with respect to time or increased respiratory frequency and tidal volume product. It can manifest itself in the form of hyperpnea, where individuals take deeper breaths which correlates with increased tidal volume, tachypnea shown in FIGS. 15E–15H which is an increased rate, without increased tidal volume or some combination of hyperpnea and tachypnea as in the examples illustrated in 14F–14J. With hyperventilation, there is an increase in the magnitude and phase difference between external and nasal flow, but the differences are minor in comparison to an obstruction as illustrated in FIGS. 14A–14J. This suggests that the increase in the amplitude of the composite waveform as shown in FIG. 14I, is principally the result of gas compression and airway resistance in the airway, rather than a simple effect of respiratory drive. In fact, an increase in respiratory frequency alone, without a change in tidal volume, results in negligible effect on the composite waveform, as shown in FIGS. 15A–15H. Therefore, airway obstruction can be differentiated from increased respiratory drive and ventilation, without obstruction, using the methodology of the present invention.

Referring to FIGS. 12K–12P the external sensor signal is normalized to nasal flow for the purposes of calibration. In contrast, referring to FIGS. 16A–16F the external sensor is used without normalization to nasal flow. The results, in terms of the composite waveforms that results from the subtraction in the time domain between the external and the nasal flow signal, are similar with and without normalization for the purposes of calibration. An airway obstruction is apparent as is the response to bronchodilation. Thus, the methodology of the present invention has a further advantage as a system that incorporates a direct measure of phase differences, i.e., the use of any external sensor with high frequency response compared with any measure of true flow (for example, pneumotachography, breath sounds), can give meaningful resultssince the phase differences still persist. This allows some measure of airway obstruction with a number of sensors with or without conventional calibration.

The importance of comparing the external and flow signals in the same time domain is germane to the measurement of impedance during exercise or hyperventilation since phase mismatch is relevant. In the horse for example, inertance (the kinetic energy for acceleration of flow) is a major component of impedance (the ratio of driving pressure to flow) during exercise, and the continuous waveform analysis of the present invention allows one to visualize the phase delay during exercise and hyperventilation that in part reflects inertance. This appears as a very early spike in the composite waveform. Without a comparison of external and nasal flow signals in the same time domain, transient phenomena of gas compression or inertance can not be visualized or analyzed. A measure of inertance is important as there are many obstructive or anatomical disorders or extrinsic devices that impose additional inertance on the respiratory system, altering lung function. During exercise, respiratory drive and ventilation are matched, but there is still the presence of inertance, reflected in a slight growing phase delay and differences in amplitude between the external and nasal flow signals, resulting in early spikes in the composite waveform, which may have diagnostic value.

In the instance where there is an increase in functional residual capacity (FRC) or residual volume (for example, air trapping during asthma or chronic obstructive pulmonary disease, emphysema, pneumothorax, positive end-expiratory pressure during ventilation), the subject's respiratory drive will be stimulated in most cases and respiratory drive to ventilation ratio will increase. However, in cases where respiratory drive does not increase to a significant extent due to physical limitations of the subject (for example, diaphragmatic muscle fatigue, weak muscles), a phase lag may persist between external and true flow and the composite and overlapping waveforms will reveal evidence of compressed gas in the thorax. The present invention may thus offer the advantage of detecting changes in FRC in instances where it was not possible to detect using prior art methodologies.

Figure 17:
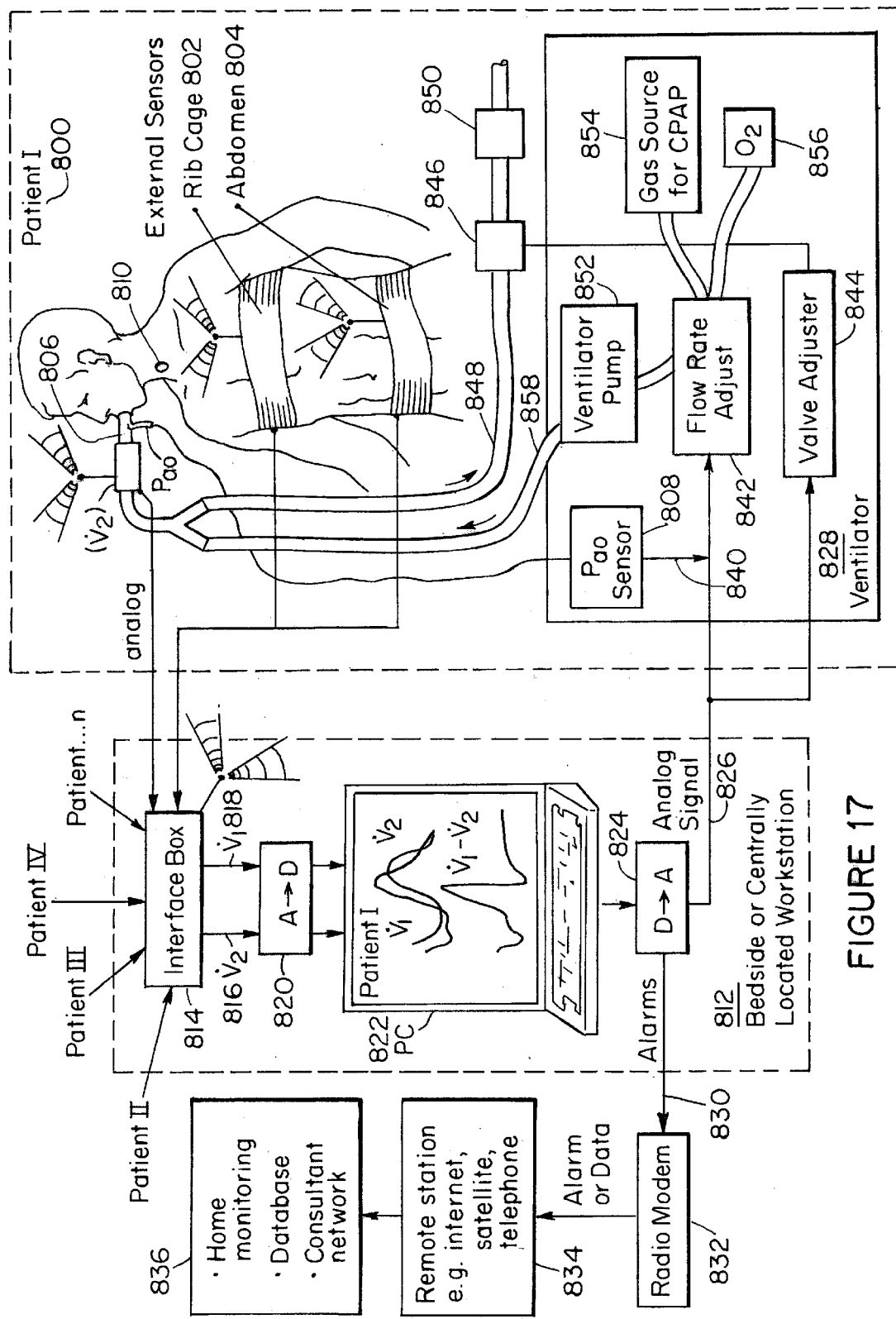
FIG. 17 is a schematic diagram of a monitoring system for a patient incorporating the method for measuring respiratory function in accordance with the present invention.

Referring to FIG. 17, a schematic diagram of a monitoring system for a human patient incorporating the method for measuring respiratory function in accordance with the present invention is illustrated. Humans breathe through their mouth and nose while some animals such as horses are solely nasal breathers, which simplifies flow collection and necessitates a different face mask for each category of subject. Humans voluntarily change breathing patterns. In animals data must be collected during tidal breathing or during physical pharmacological provocation to change the breathing pattern. Further, animals are quadripeds and body posture in animals is not likely to change as drastically as in sitting or in the supine posture in humans. Animals in some cases have much greater abdominal contribution versus a rib or chest contribution, therefore signals emanating from the abdomen may be useful to compare with flow. A signal collected from the abdomen in horses represents a total effort required for breathing and reflects diaphragmatic movement and elastic recoil. In humans, data collected from the abdomen and rib maybe similar or one signal may predominate over the other. The human patient, patient I 800, has external sensors to measure effort applied to the rib cage 802 and abdomen 804. The patient I 800 is also equipped with an endotracheal tube 806 or other patient and ventilator interface such as a continuous positive airway pressure (CPAP) mask. The airway flow of the patient is measured by a sensor 808 positioned at the airway opening such as a pneumotachograph that is coupled to the endotracheal tube 806. The sensor 808 may also be integral with the CPAP mask. In the alternative, a breath sound sensor 810, may be used to record sound as a surrogate for a measure of flow at the airway opening. This is another unobtrusive method to measure airway flow. Sound measured in decibels at a prescribed frequency versus time resembles flow. Since the output variables of interest for the present invention are principally kinetic (phase related), any measure of flow may be used such as sound, with post-hoc calibration or no calibration. Sound could be recorded using a small microphone in contact with the skin surface overlaying the trachea, lung or any segment of the respiratory system or by placing a directional microphone in the stream of air flow. Appropriate amplification, analog to digital conversion and waveform production is required for comparison with effort.

The signals indicative of effort as measured by, for example RIP bands at the rib cage 802 and abdomen 804, and the signal indicative of airflow form inputs into a beside or centrally located workstation 812, in particular into an interface box 814 of the workstation. The interface box 814 may receive data indicative of effort and airflow from a plurality of patients whose respiration is being controlled from the bedside or centrally located workstation 812. The interface box, upon receiving the effort and flow signals from the patient then amplifies and transmits the signals. The outputs 816, 818 of the interface box then form inputs into an analog to digital converter 820. Processing of the effort and flow signals then occurs in the processor/display 822 in accordance with the present invention as described hereinbefore. Essentially a comparison of the effort and flow signals is performed by either overlapping the signals and studying the waveform differences visually or by generating a composite waveform indicative of the analog or digital point-by-point subtraction of the flow signal from the effort signal. The displayed overlapped and composite waveforms provide for efficient monitoring of the respiratory function by a health care provider as they need only to visually monitor the state of the respiratory function of the patient by either inspecting the overlapped or composite waveform or a combination of both.

The output of the processor/display 822 is then converted to an analog signal in a digital to analog converter 824 which supplies an analog signal 826 to a ventilator 828 or an alarm signal 830 via a radio modem 832 to a remote station 834. The remote station may be coupled to a network 836 which may be used for home monitoring of a patient, to a database system for storing of data and any post-acquisition analysis or trending, or to a network used by consultants also for further analytical processing.

The analog signal 826 that is outputted from the bedside or centrally located workstation 812 incorporating the system to measure respiratory function, in conjunction with the output 840 of the airflow sensor 808, form inputs to a flow rate adjuster 842 of the ventilator 828. The analog signal also forms an input into a ventilator valve adjuster 844 which in turn adjusts an exhalation valve 846 located on the exhalation segment 848 of the ventilator tubing. An exhalation flowmeter or volume sensor 850 is located downstream of the exhalation valve. The exhalation flowmeter 850 provides a check of the ventilation system against system leaks by checking if the amount of gas inputted by the ventilator is equivalent to the amount exhaled. The analog signal 826 indicative of the difference between the effort and airflow signal affects the CPAP flow rate and the resistance of the exhalation valve 846 to increase or decrease CPAP or change the oxygen percentage supplied to the patient requiring assist ventilation. Thus, the ventilator pump 852 provides, using the continuous fresh gas source for CPAP 854 and an oxygen source 856, the required amount of oxygen to the patient via the inhalation segment 858 of the ventilation tubing.

The present invention lends itself to many applications. It can be used as a treadmill exercise monitoring system which requires hard wiring of the subject. Alternatively, a remote telemetric system can use radio waves to transmit effort-flow data to a workstation for real-time monitoring, display, data recording or processing. This application during an exercise regiment pertains to both animals and humans. The advantage of the present invention effort-flow system is the lack of obtrusiveness and allowing the subject to adopt natural body posture for exercise and sports. For example, in racehorses, body posture and breathing coordination, and head-neck angle are critical in optimizing respiratory and hence athletic performance.

A second application of the present invention is continuous or intermittent home or hospital monitoring for adults, children, infants and animal subjects as illustrated in FIG. 17. For example, patients on ventilators who require CPAP, assisted ventilation or synchronized/spontaneous intermittent mandatory ventilation SIMV, where effort is involved can use the present invention. Further, persons at home with severe respiratory disease and/or episodic disease which requires continuous or intermittent monitoring and alarm feedback for conditions such as emphysema, asthma, COPD, cystic fibrosis etc. The apparatus of the present invention may be tied in with an oxygen delivery system. The present invention provides a good effort to flow indication which can be correlated to the demand for oxygen thus making it attractive to tie the present invention to an oxygen delivery system. Further, an alarm system, utilizing preset thresholds and criteria can be optionally incorporated into the present invention. In patients on ventilators, inspiratory pressures are monitored and the present invention may allow monitoring of expiratory effort which is a good reflection of small airway flow limitations during ventilation. In patients with dynamic hyperinflation and growing FRC, the present invention may detect increased gas compression without change or before worsening airway obstruction, for example, in emphysema, asthma or COPD.

The present invention also provides a test to replace the peak-flow meter since the effort-flow kinetics during forced maneuvers requires a maximum or submaximum expulsion of air. Many severely effected patients cannot perform maximal forced maneuvers due to chest wall disease or dyspnea. An example of the value of the present invention in this regard is in the setting of a pneumothorax which occurs naturally or subsequent to surgery that is invasive to the lung and chest wall; the present invention compliments blood gas analysis, imaging, radiology and can cut costs of these procedures.

A bedside system with RIP or other bands, pneumotachograph, transducers, preamplifiers and simple liquid crystal displays (LCD) provides specific hospital needs. This introduces a greater degree of hardware uniqueness since all electrical components are housed in one unit and connected together on a circuit board.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for measuring respiration function of a living organism, comprising the steps:

obtaining a first input signal from a first sensor indicative of a change in lung volume during breathing by said living organism;

obtaining a second input signal from a second sensor indicative of airflow through the respiratory system of said living organism during the change in lung volume; and processing said first input signal and said second input signal to calculate a third signal indicative of respiratory restriction of said living organism.

2. The method according to claim 1, wherein the processing step comprises the step of comparing said first input signal to said second input signal.

3. The method according to claim 2, wherein the step of comparing said first and second input signals comprises analyzing phase and magnitude differences between said first and second signals in the same time domain.

4. The method according to claim 3, further comprises determining the location of respiratory restriction by analyzing whether the phase and magnitude differences occur in one of an inspiratory portion of said first and second signals and an expiratory portion of said first and second signals.

5. The method according to claim 4, wherein the phase and magnitude differences in the inspiratory portion of said first and second signals indicate a proximal respiration restriction in a region such as the upper airways of the organism.

6. The method according to claim 4, wherein the phase and magnitude differences in the expiratory portion of said first and second signals indicate a distal respiration restriction in a region such as the lower airways of the organism.

7. The method according to claim 3, wherein the step of comparing said first and second input signals further comprises the step of subtracting said second input signal from said first input signal in the same time-domain.

8. The method according to claim 1, further comprising of obtaining the first input signal through use of respiratory induction plethysmography.

9. The method according to claim 1, further comprising of obtaining the first input signal through use of a piezoelectric device.

10. The method according to claim 1, further comprising of obtaining the second input signal through use of a pneumotachographic measurement device.

11. The method according to claim 1, further comprising the step of calibrating first input signal.

12. The method according to claim 1, further comprising the step of displaying said first input signal and said first second input signal as digital waveforms.

13. The method according to claim 1, further comprising the steps of:

obtaining a signal through respiratory inductance plethysmography of a chest of said living organism;

obtaining a signal through respiratory inductance plethysmography of an abdomen of said living organism;

summing said chest signal and said abdomen signal to form said first input signal;

converting said first input signal from an analog signal to a digital signal;

taking the derivative of said digital first input signal;

converting said second signal from an analog to a digital signal; and subtracting said second input signal from said digital derivative of first input signal to obtain said third signal.

14. The method according to claim 13, wherein the steps of converting, an input signal from analog to digital signal, taking the derivative of, converting signal from an analog to digital signal and subtracting said second input signal from digital derivative of first input signal, uses at least one of the signal of the chest, the signal of the abdomen or the first input signal indicative of the sum of the chest and abdomen signal.

15. An apparatus for obtaining a signal indicative of respiration of a living organism, comprising:
  a first sensor device that obtains a first input signal indicative of a change in lung volume during breathing by said living organism, the first sensor device including a sensor adapted to be positioned on an external surface of the living organism;
  a second sensor device that obtains a second input signal indicative of actual airflow through the respiratory system of said living organism; and
  a processing device that processes said first input signal and said second input signal to calculate a third signal indicative of respiration restriction of said living organism.

16. The apparatus according to claim 15, wherein said processing device compares said first input signal from said second input signal to analyze phase and magnitude differences between said input signals.

17. The apparatus according to claim 15, wherein said first device comprises a respiratory inductance plethysmography measurement device.

18. The apparatus according to claim 15, wherein said first device comprises a piezoelectric measurement device.

19. The apparatus according to claim 15, wherein said first device comprises an impedance plethysmography measurement device.

20. The apparatus according to claim 15, wherein said second device comprises a pneumotachographic measurement device.

21. The apparatus according to claim 15, wherein said second device comprises an ultrasonic measurement device.

22. The apparatus according to claim 15, wherein said second device comprises a thermistor measurement device.

23. The apparatus according to claim 15, further comprising a calibration device for calibrating said first input signal.

24. The apparatus according to claim 15, further comprising a calibration device for calibrating said second input signal.

25. The apparatus according to claim 15, further comprising an interface device for providing said first and second input signals to the processing device.

26. The apparatus according to claim 25, wherein the interface device further comprises a summer, a differentiator and a filter.

27. The apparatus according to claim 15, further comprising a device for displaying said first input signal and said second input signal as digital waveforms.

28. The apparatus according to claim 15, further comprising a device for displaying first input signal and said second input signal as analog waveforms.

29. The apparatus of claim 15, wherein the processing device comprises a programmable computer having a memory, the memory having stored referenced data.

30. The apparatus of claim 15, wherein the apparatus weighs less than fifteen (15) pounds.

31. A method for measuring respiration function of a living organism, comprising the steps:
  obtaining a first input signal from a first sensor indicative of effort required to breathe by said living organism;
  obtaining a second input signal from a second sensor indicative of airflow through the respiratory system of said living organism; and
  comparing said first input signal and said second input signal by analyzing phase and magnitude differences between said first and second signals in the same time domain to form a third signal indicative of respiratory restriction of said living organism.

32. The method according to claim 31 further comprises determining the location of respiratory restriction by analyzing whether the phase and magnitude differences occur in one of an inspiratory portion of said first and second signals and an expiratory portion of said first and second signals.

33. The method according to claim 32 wherein the phase and magnitude differences in the expiratory portion of said first and second signals indicate a distal respiration restriction in a region such as the lower airways of the organism.

34. The method according to claim 31 wherein the phase and magnitude differences in the inspiratory portion of said first and second signals indicate a proximal respiration restriction in a region such as the upper airways of the organism.

35. The method according to claim 31 wherein the step of comparing said first and second input signals further comprises the step of subtracting said second input signal from said first input signal in the same time-domain.

36. The method according to claim 31 further comprising of obtaining the first input signal through use of respiratory induction plethysmography.

37. The method according to claim 31 further comprising of obtaining the first input signal through use of a piezoelectric device.

38. The method according to claim 31 further comprising of obtaining the second input signal through use of a pneumotachographic measurement device.

39. The method according to claim 31 further comprising the step of calibrating first input signal.

40. The method according to claim 31 further comprising the step of displaying said first input signal and said first second input signal as digital waveforms.

41. The method according to claim 31 further comprising the steps of.
  obtaining a signal through respiratory inductance plethysmography of a chest of said living organism;
  obtaining a signal through respiratory inductance plethysmography of an abdomen of said living organism;
  summing said chest signal and said abdomen signal to form said first input signal;
  converting said first input signal from an analog signal to a digital signal;
  taking the derivative of said digital first input signal;
  converting said second signal from an analog to a digital signal; and
  subtracting said second input signal from said digital derivative of first input signal to obtain said third signal.

42. The method according to claim 41 wherein the steps of converting, an input signal from analog to digital signal, taking the derivative of, converting signal from an analog to digital signal and subtracting said second input signal from digital derivative of first input signal, uses at least one of the signal of the chest, the signal of the abdomen or the first input signal indicative of the sum of the chest and abdomen signal.

43. An apparatus for obtaining a signal indicative of respiration of a living organism, comprising:

a first device that obtains a first input signal indicative of effort required to breathe by said living organism;

a second device that obtains a second input signal indicative of actual airflow through the respiratory system of said living organism;

a processing device that compares said first input signal and said second input signal by analyzing phase and magnitude differences between said first input signal and said second input signal; and forming a third signal indicative of respiration restriction of said living organism.

44. The apparatus according to claim 43 wherein said first device comprises a respiratory inductance plethysmography measurement device.

45. The apparatus according to claim 43 wherein said first device comprises a piezoelectric measurement device.

46. The apparatus according to claim 43 wherein said first device comprises an impedance plethysmography measurement device.

47. The apparatus according to claim 43 wherein said second device comprises a pneumotachographic measurement device.

48. The apparatus according to claim 43 wherein said second device comprises an ultrasonic measurement device.

49. The apparatus according to claim 43, wherein said second device comprises a thermistor measurement device.

50. The apparatus according to claim 43 further comprising a calibration device for calibrating said first input signal.

51. The apparatus according to claim 43 further comprising a calibration device for calibrating said second input signal.

52. The apparatus of claim 43 further comprising an interface device for providing said first and second input signals to the processing device.

53. The apparatus of claim 43 wherein the interface device further comprises a summer, a differentiator and a filter.

54. The apparatus of claim 43 further comprising a device for displaying said first input signal and said second input signal as digital waveforms.

55. The apparatus according to claim 43 further comprising a device for displaying first input signal and said second input signal as analog waveforms.

56. The apparatus of claim 43, wherein the processing device comprises a programmable computer having a memory, the memory having stored referenced data.

57. The apparatus of claim 43 wherein the apparatus weighs less than fifteen (15) pounds.

* * * * *